US006544229B1

United States Patent
Danby et al.

(10) Patent No.: US 6,544,229 B1
(45) Date of Patent: Apr. 8, 2003

(54) LINEARLY MOTILE INFUSION PUMP

(75) Inventors: Hal C. Danby, Sudbury (GB); John Hawker, Hadleigh (GB)

(73) Assignee: Baxter International Inc, Deerfield, IL (US)

(*) Notice: Subject to any disclaimer, the term of this patent is extended or adjusted under 35 U.S.C. 154(b) by 0 days.

(21) Appl. No.: 09/561,789

(22) Filed: May 1, 2000

(51) Int. Cl.[7] ................................................. A61M 5/00
(52) U.S. Cl. ........................ 604/154; 604/151; 604/131; 60/527
(58) Field of Search .................................. 604/154, 155, 604/152, 151, 131, 67; 60/527

(56) References Cited

U.S. PATENT DOCUMENTS

| 266,107 A | 10/1882 | Curtiss |
| 311,783 A | 2/1885 | Rau et al. |
| 640,868 A | 1/1900 | Bring |
| 2,183,482 A | 12/1939 | Kurkjian |
| 3,886,938 A | 6/1975 | Szabo et al. |
| 4,320,757 A | 3/1982 | Whitney et al. |
| 4,529,401 A | 7/1985 | Leslie et al. |
| 4,648,812 A | 3/1987 | Kobayashi et al. |
| 4,650,469 A | 3/1987 | Berg et al. |
| 4,668,220 A | 5/1987 | Hawrylenko |
| 4,731,058 A | 3/1988 | Doan |
| 4,741,732 A | 5/1988 | Crankshaw et al. |
| 4,908,017 A | 3/1990 | Howson et al. |
| 4,943,279 A | 7/1990 | Samiotes et al. |
| 5,000,739 A | 3/1991 | Kulisz et al. |
| 5,106,372 A | 4/1992 | Ranford |
| 5,176,004 A | 1/1993 | Gaudet |
| 5,222,362 A | 6/1993 | Maus et al. |
| 5,263,323 A | 11/1993 | Maus et al. |
| 5,279,556 A | 1/1994 | Goi et al. |
| 5,312,389 A * | 5/1994 | Theeuwes et al. ...... 604/141 X |
| 5,389,078 A | 2/1995 | Zalesky et al. |
| 5,395,320 A | 3/1995 | Padda et al. |
| 5,411,489 A | 5/1995 | Pagay et al. |
| 5,478,211 A | 12/1995 | Dominiak et al. |
| 5,482,446 A | 1/1996 | Williamson et al. |
| 5,505,706 A | 4/1996 | Maus et al. |
| 5,522,799 A | 6/1996 | Furukawa |
| 5,540,665 A * | 7/1996 | Mercado et al. ............ 604/145 |
| 5,593,387 A | 1/1997 | Rupp |
| 5,637,093 A | 6/1997 | Hyman et al. |
| 5,658,250 A | 8/1997 | Blomquist et al. |
| 5,683,367 A | 11/1997 | Jordan et al. |
| 5,695,473 A | 12/1997 | Olsen |
| 5,738,658 A | 4/1998 | Maus et al. |
| 5,795,327 A | 8/1998 | Wilson et al. |
| 5,842,841 A | 12/1998 | Danby et al. |
| 5,876,370 A | 3/1999 | Blomquist |
| 5,897,530 A | 4/1999 | Jackson |
| 5,954,696 A | 9/1999 | Ryan |
| 5,964,583 A | 10/1999 | Danby |
| 6,013,057 A | 1/2000 | Danby et al. |
| 6,039,251 A | 3/2000 | Holowko et al. |

OTHER PUBLICATIONS

Medex, Specifications for the Medfusion 2010i Syringe Pump, Revision 1/99.

* cited by examiner

*Primary Examiner*—Kevin Lee
(74) *Attorney, Agent, or Firm*—Richard Himelhoch; Wallenstein & Wagner Ltd.

(57) ABSTRACT

An ambulatory infusion pump (10) has a syringe barrel (16) having a fluid chamber (19) and an inner wall (22). The pump (10) further has an infusion engine (14) for moving fluid through the syringe barrel (16). The infusion engine (14) has a member (42) for engaging a portion of the syringe barrel (16) for moving the engine (14) linearly along the syringe barrel (16).

67 Claims, 15 Drawing Sheets

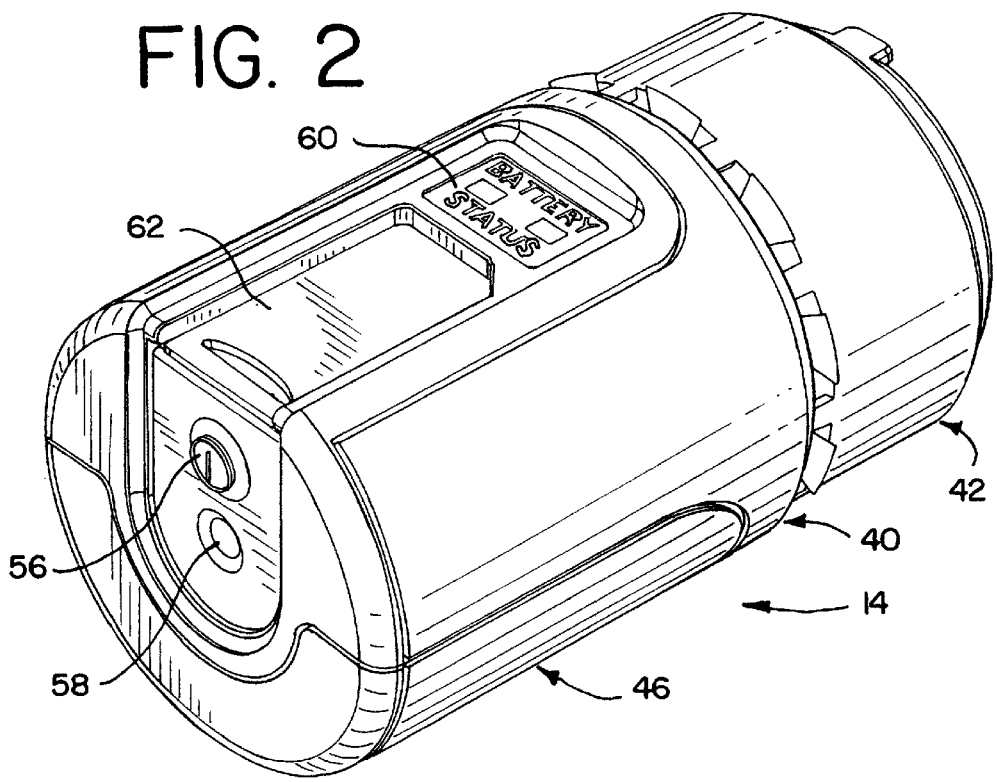
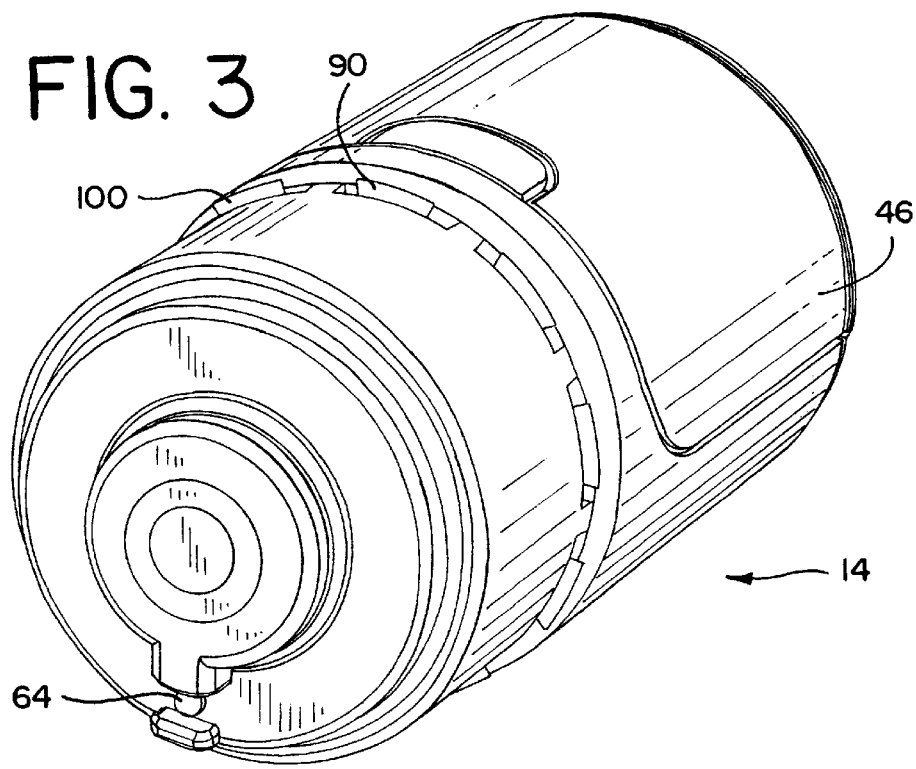

INFUSION CYCLE START

INFUSION CYCLE START

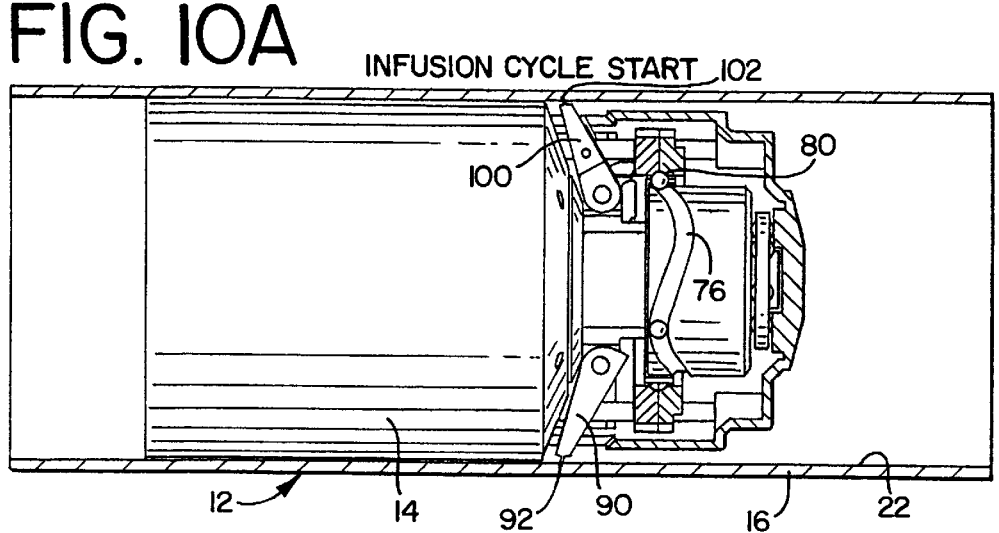
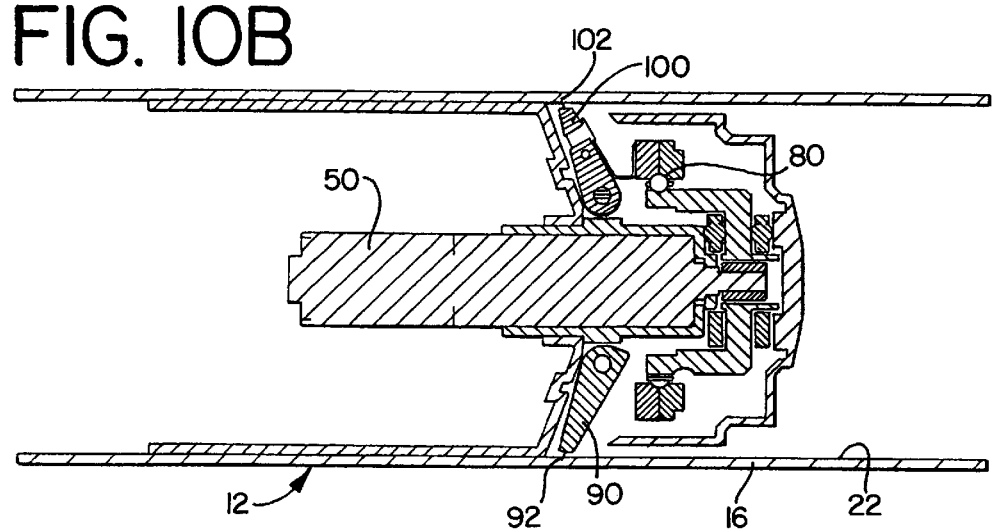
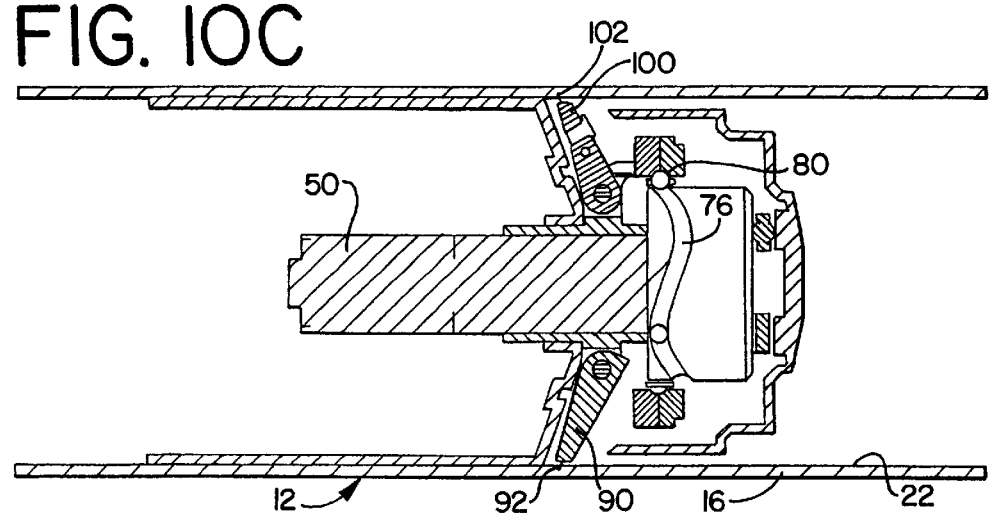

INFUSION CYCLE END

FIG. 12A  INFUSION CYCLE END
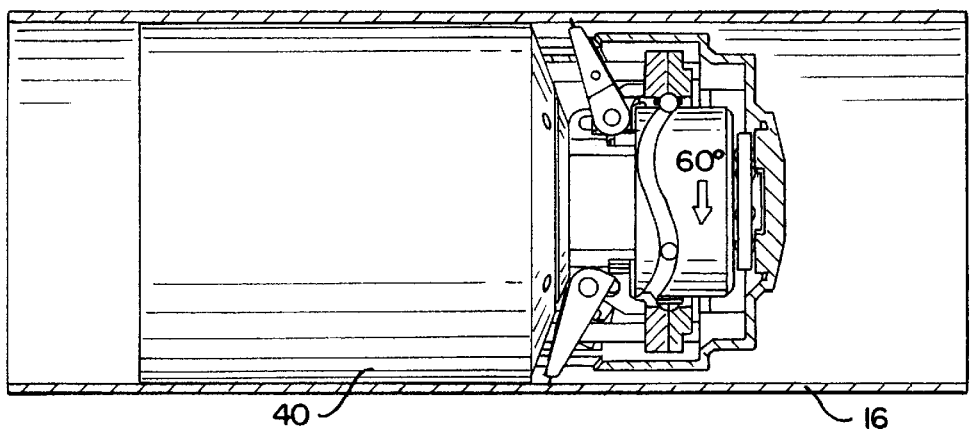
FIG. 12B
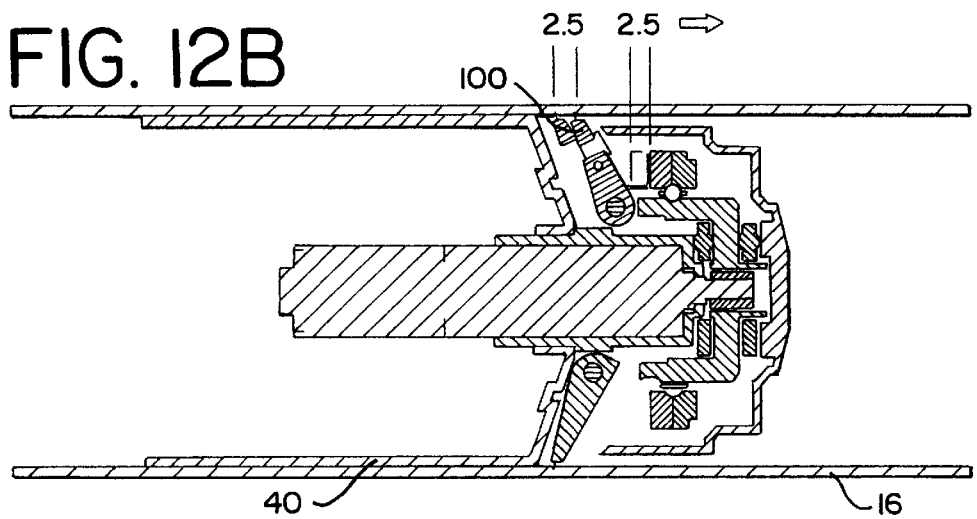
FIG. 12C
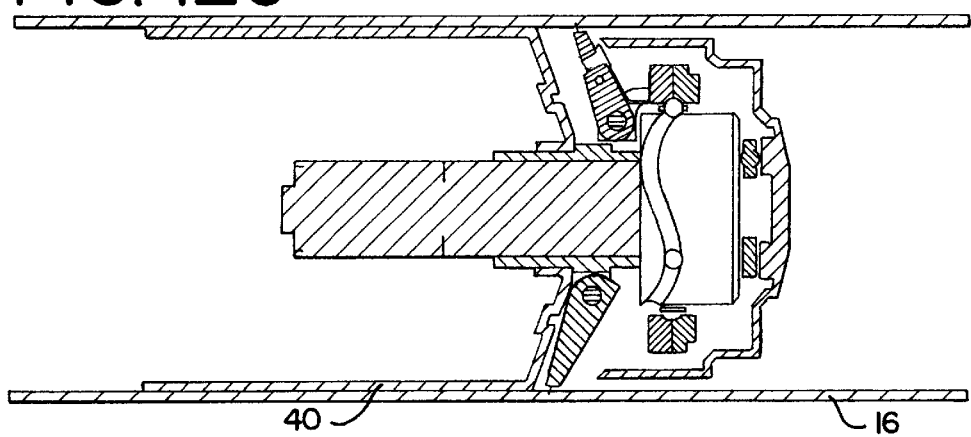

LINEARLY MOTILE INFUSION PUMP

TECHNICAL FIELD

The present invention relates to a medical pump and, more particularly, to an ambulatory infusion pump.

BACKGROUND OF THE INVENTION

Oftentimes, medical patients require precise delivery of continuous medication or at set periodic intervals. Certain liquid medicaments, or drugs, however, rarely achieve their maximum therapeutic action through conventional injection techniques. And, many drugs reach their full potential only through precise delivery over an extended period of time. Medical pumps have been developed to provide controlled drug infusion through the pump wherein the drug can be administered at a precise rate that keeps the drug concentration within the therapeutic margin and out of a possible toxic range with certain drugs. The medical pumps provide appropriate drug delivery to the patient at a controllable rate which does not require frequent medical attention. The medical pumps further facilitate administration of intravenous therapy to patients outside of a clinical setting. In addition, doctors have found that in many instances patients can return to substantially normal lives, provided that they can receive periodic or continuous intravenous administration of medication. These factors have combined to promote the development of increasingly lightweight, portable or ambulatory infusion pumps that can be worn by a patient and are capable of administering a continuous supply of medication at a desired rate.

A wide variety of ambulatory pumps in use in the medical field are intended to meet the need of a high degree of accuracy in the administration of fluids to maximize the effectiveness of medication and to protect the patient. Typically, these ambulatory infusion pumps include a pump control unit and a drive mechanism including a variety of operating controls adapted to accept a disposable pump chamber assembly. The pump chamber assembly has an inlet end connected to a liquid reservoir and an outlet end connected to an I.V. tube that in turn is connected for intravenous administration to a patient by a cannula.

Often, the same medical pump is programmable to allow for different pump application programs for pumping different therapeutics to a patient, such as antibiotic therapy, chemotherapy, pain control therapy, and nutritional therapy, etc. With regard to pain control therapy, medical infusion pumps are typically used for the management of acute pain, frequently in a hospital setting. These pumps deliver morphine or other analgesics to the patient, according to a pre-programmed prescription controlled by the pump. These pumps generally include various modes of infusion, such as a continuous mode in which the liquid medicament is continuously infused at a constant rate, or a ramp mode in which the rate of infusion gradually increases, then remains constant, and then gradually decreases. Further, these pumps include the capability for patient demand dosing. Typically, pain control therapy utilizing pumps having patient demand dosing capabilities is referred to as "PCA" or patient controlled analgesia.

With PCA, it is critical to carefully track the amount of drug a patient has received, the number of times the patient has requested additional demand doses, and the number of demand doses actually delivered to the patient, along with other information. Such historical information is utilized to adjust or "titrate" the patient's prescription. For such purposes, PCA infusion pumps have a non-volatile memory in which infusion parameters may be stored and from which such parameters may be retrieved. U.S. Pat. No. 5,181,910 discloses an infusion pump that is programmable and has an integral controller for automatically controlling and determining the interval between pump activations necessary to produce a substantially linear rate of increase or decrease in liquid flow during the administration of liquid medicament to a patient. The integral controller is a keypad on the face of the pump having keys which a clinician manually depresses to program the pump. These pumps also have a non-volatile memory in which such pump-specific infusion parameters may be stored and from which such parameters may be retrieved.

Typical parameters that these pumps, which have integral processors or controllers, are able to control include: the rate at which the medicament is infused, the volume or dosage of medicinal fluid administered, whether the drug is delivered as a bolus or continuous infusion, the time that the administration occurs, and/or the interval of time that the pump will operate. These parameters are usually entered into the electronic non-volatile memory of the pump controller via a user interface control panel on the pump (i.e., a keypad on the face of the pump). Although entry of the pump-specific parameters that control the pump's operation may be relatively straightforward, several minutes may be required to specify all of the data required to define a drug delivery protocol. More important, each time that a pump is programmed to administer a specific medicinal fluid, there is a risk that human error may cause improper values for the parameters to be entered.

In addition to historical "pump-specific" information, additional "patient-specific" information is required for the patient's medical chart. Thus, adequate monitoring of the drug pump and the patient's usage of the drug pump, along with monitoring of the patient, is still required. The combination of infusion data (i.e., "pump-specific" information) and patient data (i.e., "patient-specific" information) is necessary to generate a complete historical record or patient chart.

U.S. Pat. No. 5,795,327, owned by the Assignee of the present invention, discloses an infusion pump with historical data recording capabilities. The pump includes a controller integral with the pump to cause the pump to deliver a plurality of infusions of liquid medicament during the infusion period, each of the infusions being made at a specific time period and flow rate, and a keypad to allow a clinician to input the program parameters into the pump. The apparatus has a nonvolatile memory and means for storing infusion data in the non-volatile memory to generate a complete historical record of the "pump-specific" data including data regarding the infusions delivered during the infusion period. The "pump-specific" infusion data stored in the non-volatile memory may include programmed infusion data manually inputted to the infusion apparatus by a clinician during programming of the apparatus through the integral keypad controller. Such manually programmed infusion data may include data representing the infusion mode, the infusion flow rate, the volume to be infused, and the infusion start time. The infusion data may also include resulting data, including data representing the time at which each infusion was made during the infusion period and the flow rate at which of each infusion was made.

In addition to storing infusion data, the pump automatically records additional real-time infusion data (i.e., more "pump-specific" information). Such data includes the times at which the run and hold keys of the pump to control the infusion were pressed by the user, the time at which the bolus-request key was pressed, including bolus requests for PCA demand dosing, whether the bolus infusion was made as requested, the time at which any alarms or malfunctions occurred, data representing the type of alarm or malfunction, and data relating to the infusion modes which were locked out, if such means are available.

Automatic recording of the "pump-specific" infusion data described above in the non-volatile memory during the manual programing and operation of the infusion apparatus allows the operator to generate a historical data record of the apparatus. This data can later be retrieved from the non-volatile memory and used for various purposes, including clinical purposes, and to confirm that the prescribed infusion was actually delivered.

Additionally, U.S. Pat. No. 5,795,327 discloses the ability of the pump to present the patient with a plurality of questions to be answered by the patient. The questions are displayed on a screen on the face of the pump, and the answers are input through the keypad on the face of the pump adjacent the display. The answers are stored in the pump's non-volatile memory. Typically, the questions may be related to the current health of the patient, and/or to the patient's health history. The infusion apparatus may have a non-volatile memory in which a plurality of question sets are stored, and the questions asked of the patient may be taken from one of the question sets which is selected based on a parameter relating to the type of infusion the patient is to receive, or has just received. These question sets are manually inputted into the infusion apparatus by a clinician during programming of the apparatus through an integral keypad on the pump.

Many concerns arise in connection with the operation of the drug pumps and with the collection and merging of data to produce a complete and accurate patient chart. One concern arises in the monitoring of the drug pump. Another concern arises in monitoring the accurate running of the software stored in the pump. Another concern arises in loading and controlling the different pump application programs for operating the pump. Another concern arises in obtaining data feedback from the drug pump. Another concern arises in communicating the data feedback from the drug pump to the patient's chart. Another concern arises in merging pump is data with patient-specific data.

Additional concerns arise in controlling the size and weight of the ambulatory infusion pump. As discussed, the pump must be lightweight and portable as it is designed to be worn by a patient. By wearing the pump, the patient can achieve as close to a normal lifestyle as possible while still receiving a supply of medicament as needed. Accordingly, size and weight of the pump are important. Certain syringe-based pumps have been developed for use as ambulatory infusion pumps. The syringe-based pumps require an external linkage such as a plunger rod that is connected to a plunger within the syringe. It is necessary for the plunger rod to be at least as long as the fluid chamber of the syringe so that the syringe can be completely evacuated. The linkage requires a drive mechanism positioned outside of the syringe to move the plunger. In addition, a larger case is required to house the syringe, external linkage and associated power sources. These additional components add to the overall size and weight of the pump. Yet another concern is precisely controlling the infusion rate of the pump.

The present invention is provided the solve these and other problems.

SUMMARY OF THE INVENTION

The present invention provides an ambulatory infusion pump that, in a preferred embodiment, is a syringe-based ambulatory infusion pump. The pump has a syringe having a unique self-propelled infusion engine that displaces fluid from the syringe and into an ambulatory patient.

According to one aspect of the present invention, the ambulatory infusion pump has a syringe barrel having a fluid chamber and an inner wall. The pump further has an infusion engine for moving fluid through the syringe barrel. The engine has a member for engaging a portion of the syringe barrel for moving the engine linearly along the syringe barrel.

According to another aspect of the invention, the engine is positioned entirely within the syringe barrel.

According to a further aspect of the invention, the member engages the inner wall to move the engine linearly along the syringe barrel. The member is a tine and generally comprises a plurality of circumferentially spaced tines.

According to a further aspect of the invention, the fluid chamber has a first length and the engine has a second length wherein the second length is less than the first length.

According to yet another aspect of the invention, a method is disclosed for infusing a fluid to a patient. A syringe barrel is provided having a fluid chamber and an infusion direction. An infusion engine is also provided having a member for engaging a portion of the syringe barrel. The infusion engine is positioned within the fluid chamber. The engine is driven linearly within the fluid chamber by moving the member into operative engagement with a portion of the syringe. To drive the engine, a first portion of the infusion engine is moved in the infusion direction while a second portion remains stationary to define an infusion cycle. The second portion is then moved while the first portion remains stationary to define a reset cycle.

Other features and advantages of the invention will be apparent from the following specification taken in conjunction with the following drawings.

BRIEF DESCRIPTION OF THE DRAWINGS

To understand the present invention, it will now be described by way of example, with reference to the accompanying drawings in which:

FIG. 2 is a rear perspective view of a reusable infusion engine used in the ambulatory infusion pump;

FIG. 3 is a front perspective view of the reusable infusion engine of FIG. 2;

FIGS. 10a–10c are cross-sectional views of the pump at the start of the infusion cycle;

FIGS. 12a–12c are cross-sectional views of the pump at the end of the infusion cycle;

DETAILED DESCRIPTION OF THE PREFERRED EMBODIMENT

Figure 1:
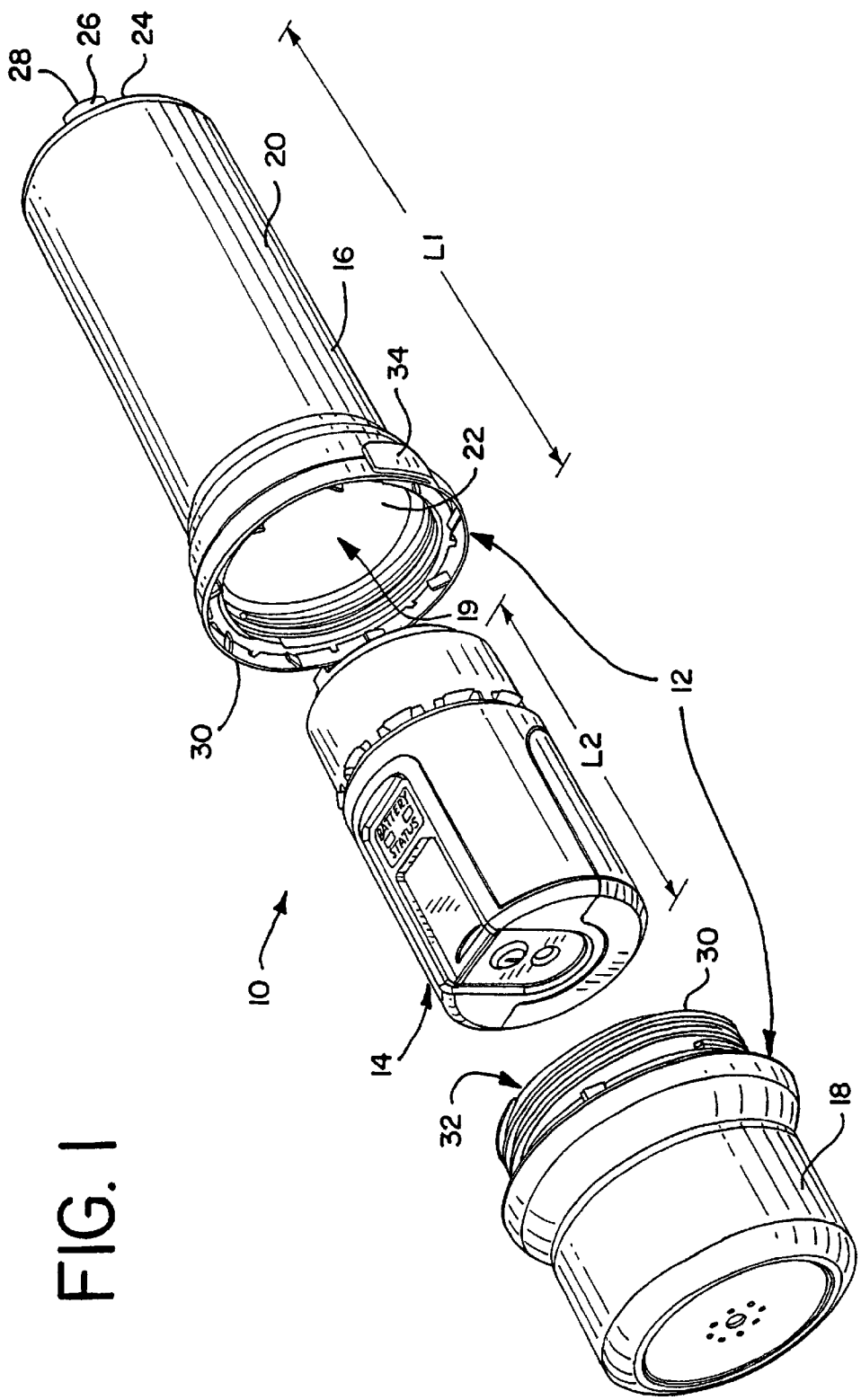
FIG. 1 is an exploded perspective view of an ambulatory infusion pump of the present invention.

While this invention is susceptible of embodiments in many different forms, there is shown in the drawings and will herein be described in detail preferred embodiments of the invention with the understanding that the present disclosure is to be considered as an exemplification of the principles of the invention and is not intended to limit the broad aspect of the invention to the embodiments illustrated.

Referring now in detail to the Figures, FIG. 1 shows an embodiment of an ambulatory infusion pump of the present invention and is generally designated with the reference numeral 10. The ambulatory infusion pump 10 generally includes a syringe assembly 12 and a reusable infusion engine 14. The structure of the ambulatory infusion pump 10 will first be described followed by a description of the operation of the pump 10.

The syringe system 12 generally includes a syringe barrel 16, a plunger 17, and a removable end cap 18. The infusion engine 14, described in greater detail below, serves as the plunger or as a drive mechanism for a separate plunger that slides along the inner wall of the syringe barrel 16 to displace medicament through the syringe 12. The syringe barrel 16 has a cylindrical outer wall 20 and inner wall 22. The syringe barrel further defines a fluid chamber 19 to contain the medication. At a first end 24, the syringe barrel 16 has a luer tip 26 having an opening 28 into the syringe barrel 16. The luer tip 26 can be equipped with a luer screw cap fitting (not shown). A second end 30 of the syringe barrel 16 is threaded to accept the end cap 18. The end cap 18 has an internal cavity 32 to accept a portion of the infusion engine 14 upon initial assembly of the pump 10. It is contemplated that the end cap 18 is an optional component but desirable and preferred to have it present. It is understood that in a preferred embodiment, the syringe system 12 utilizes a conventional syringe barrel although other types and shapes of fluid reservoirs could be utilized in the pump of the present invention.

The syringe system 12 includes a tamper evident sealing device. The device ensures that once the syringe barrel 16 has been filled with medicament, a patient or other person cannot tamper with the contents without access to the medicament being visibly apparent. To this end, a tab 34 is provided on the syringe barrel 16. The tab 34 cooperates with the end cap 18 after it is screwed onto the syringe barrel 16 such that the tab must be removed before unscrewing the end cap 18. Thus, if the tab 34 was removed, it would be evident that the patient had tampered with the pump 10. The threaded engagement between the syringe barrel 16 sand the end cap 18 provides a splash-proof seal.

Figure 4:
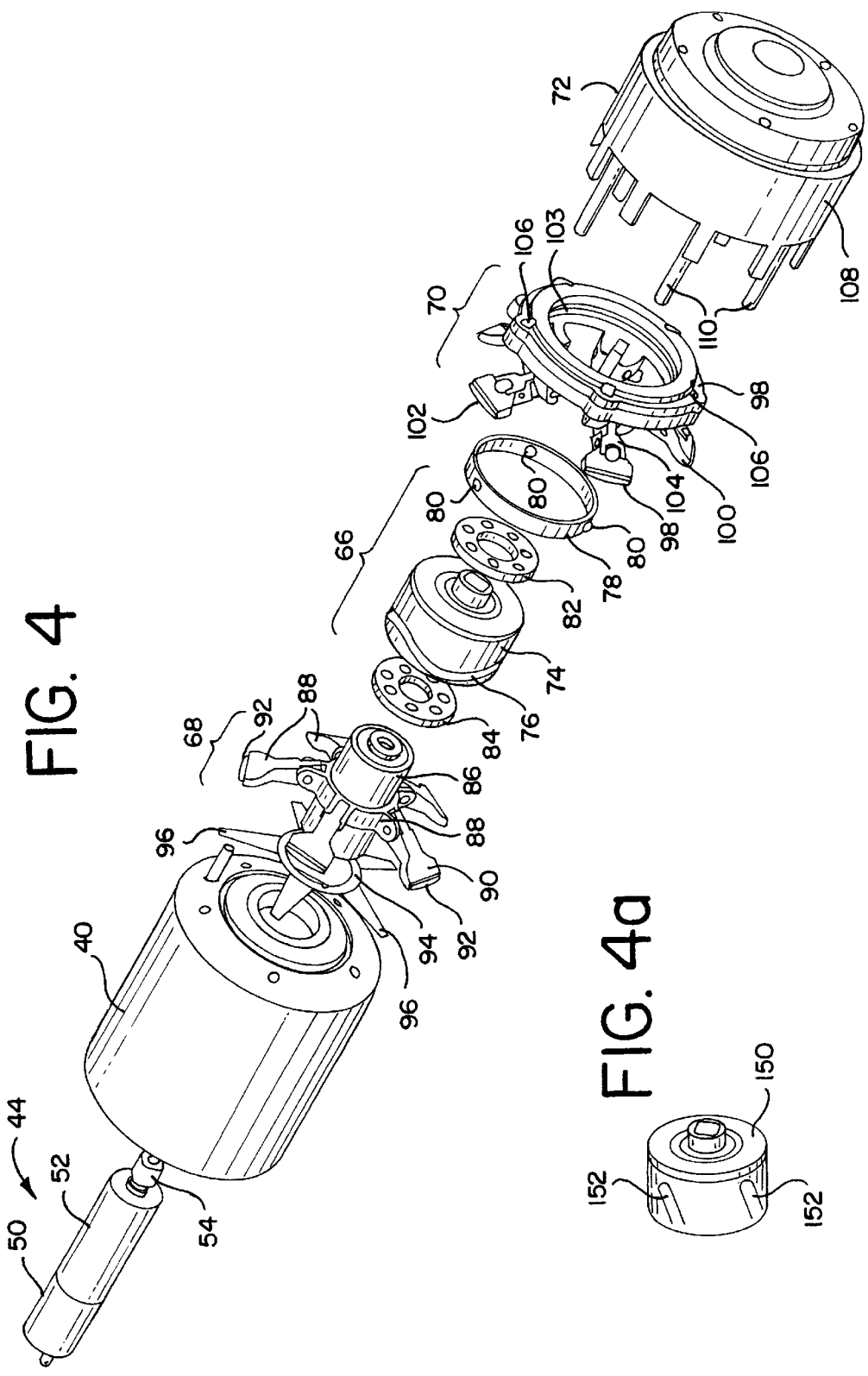
FIG. 4 is a more detailed front exploded perspective view of the pump of FIG. 1.
Figure 13:
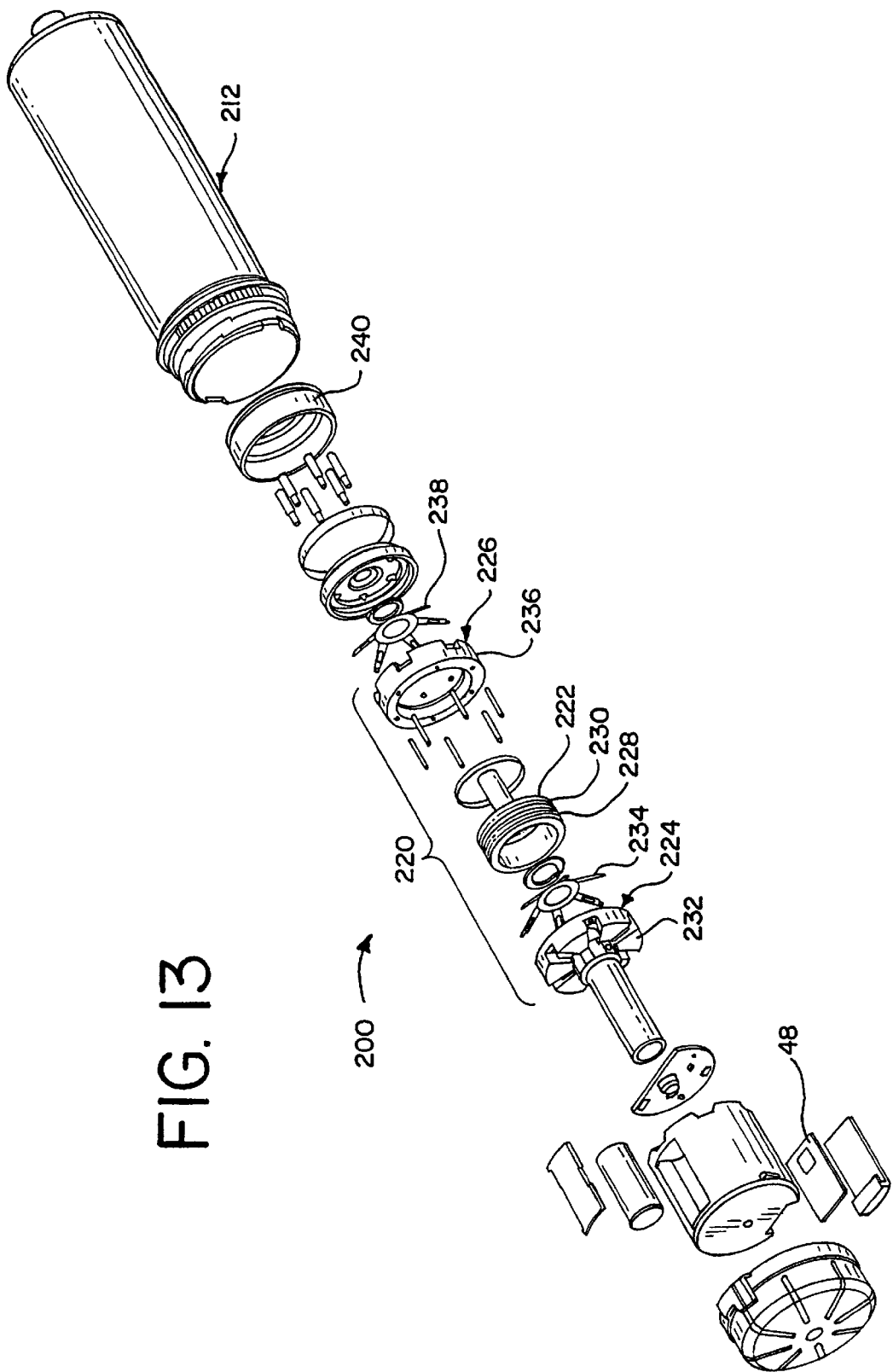
FIG. 13 is an exploded view of another embodiment of an ambulatory infusion pump of the present invention.
Figure 14:
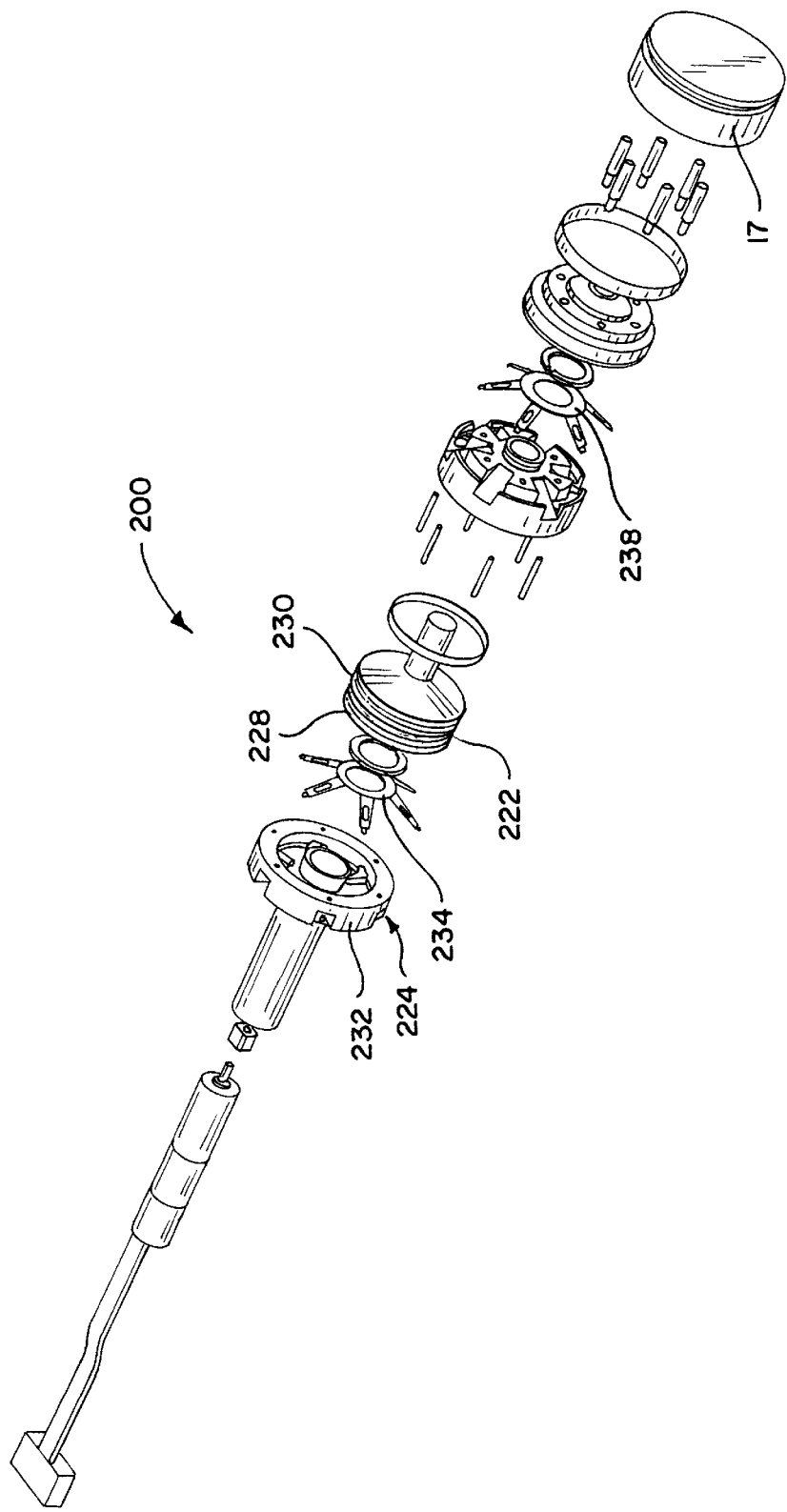
FIG. 14 is another exploded perspective view of the pump of FIG. 12.

As shown in FIGS. 2–6, the infusion engine 14 generally includes an electronics housing 40 and a pump head 42. The infusion engine 14 generally acts as the plunger for the syringe or attaches to a plunger to displace medicament through the opening 28 and associated tubing sets (not shown) to be delivered intravenously to a patient. The electronics housing 40 generally houses electronics and also includes a drive mechanism 44, power supply 46 and a programmable computer card 48 (See FIG. 13). As shown in FIG. 4, the drive mechanism 44 includes a DC motor 50 and gearbox assembly 52 used to drive the pump head 42 as described in greater detail below. The motor 50 can also have an encoder attached to the motor shaft to allow for precise monitoring and control of the motor rotation. In one preferred embodiment, the DC motor 50 is a 3 volt motor and only 10 millimeters in diameter. An electronic control circuit provides pulses of energy to the motor 50 to precisely drive the motor 50.

The gearbox assembly 52 has a drive connector 54 adapted to be connected to the pump head 42. As is shown in FIGS. 2 and 3, the electronics housing 40 further houses the power supply 46, which is preferably in the form of a rechargeable battery pack. The housing 40 is preferably made from an elastomeric material. The housing 40 has a start button 56 and an IR communications lens 58 as well as a battery charge display 60. The infusion engine 14 can also be equipped with patient demand dosing capabilities ("PCA"). The engine 14 can have a sensor incorporated therein for receiving a wireless transmission, such as by a remote control unit operated by the patient, wherein the patient can instruct the pump 10 to deliver additional medicament on demand. Such PCA steps would be monitored and logged by the smart card 44.

The housing further has a slot 62 that accepts the programmable computer card 48. The programmable computer card 44 stores algorithms and controls the actuation of the engine and, therefore, the infusion rate of the pump 10. A variety of infusion rates can be programmed into the card 44 to suit specific drug therapies. In addition, data can be uploaded to the device via an RF link. The computer card 44 can be similar to the device disclosed in U.S. Pat. No. 6,039,251 entitled "Method And System For Secure Control Of A Medical Device" which is expressly incorporated in its entirety herein by reference and made a part hereof.

As shown in FIG. 3, the housing 40 has a plunger detect sensor 64 located on its front end. As will be described in greater detail, the plunger 17 is included with the syringe 12. The sensor 64 is adapted to detect instances when the infusion engine 14 is inserted into the syringe barrel 16 but is not pushed against the plunger. This feature will be described in greater detail with respect to the operation of the pump 10.

FIGS. 4–11 show the pump head 42 in greater detail. The pump head 42 converts rotary motion of the drive mechanism 44 into linear movement of the pump head 42 and, therefore, the entire infusion engine 14. The pump head 42 generally includes a cam assembly 66, a first tine assembly 68, a second tine assembly 70, and a front shroud 72. The first tine assembly 68 and the second tine assembly 70 engage a portion of the syringe 12 to move the engine 14 along the syringe 12. The cam assembly 66 has an inner rotating ball race 74 or cam member 74. The cam member 74 has a cam groove 76. In a preferred embodiment, the cam groove 76 is generally sinusoidal in shape although it does necessarily have the same frequency as a sine wave. For example, in a preferred form of the invention the groove 76 moves through three complete up and down cycles about the circumference of the cam member 74. It is understood that the cam groove 76 could take other forms. The cam groove 76 is formed around the entire outer periphery of the cam member 74. The cam assembly 66 also has a ball bearing cage 78 carrying a plurality of ball bearings 80 radially spaced around the cage 78. In a preferred embodiment, three precision ball bearings 80 are used although it is understood that a single ball bearing 80 could be used or four or more ball bearings 80 could be used. In addition, the ball bearings 80 are stainless steel precision balls. The cage 78 fits over the cam member 74 wherein the ball bearings 80 ride within the cam groove 76. The cam assembly 66 further has first thrust bearing 82 on one end of the cam member 74 and a second thrust bearing 84 on another end of the cam member 74. The cam assembly 66 is connected at each end to the first tine assembly 68 and the second tine assembly 70 as described below.

The first tine assembly 68 has a motor housing 86 and a first tine base 88 having a plurality of engaging members, arms or tines 90 extending radially outwardly from the base 88 and being circumferentially-spaced. Each tine 90 has a blade 92 at its distal end that is adapted to engage or grip an inner surface of the syringe barrel 16. The tines 90 are pivotally connected to the base 88. In a preferred embodiment, five tines 90 are provided although more or less can be used.

The first tine assembly 68 also includes a first tine spring 94 that has arms 96 that correspond and preferably are positioned in registration with the tines 90. The spring 94 is connected to the tines 90 and biases the arms 96 toward the electronics housing 40 (in a direction opposite movement of the engine 14). The spring 94 thus pushes the tines 90 against the inner wall 22 of the syringe barrel 16 so that the blades 92 engage the inner wall 22. In one preferred embodiment, the tines 90 and spring 94 can be combined wherein the tines 90 can be integrally molded to provide a biasing spring force. It is further understood that the tines 90 could be designed to integrally incorporate the blades 92 or other structure that would adequately engage or grip the syringe 12. To that end, the syringe 12 could incorporate different structural or material properties to enhance the ability of the engine 14 to grip the syringe 12.

The motor housing 86 receives the drive mechanism 44 and is securely connected to the drive connector 54. The first tine assembly 86 is further connected to the cam assembly 66 wherein the motor housing 86 is secured within the ball race 74. As will be described below, the cam assembly 66 and first tine assembly 68 rotate via the drive mechanism 44. Thus, the first tine assembly is fixed to the drive mechanism and the tines 90 are referred to as the "fixed tines" 90. In addition, the motor housing 86 is fixed to the front shroud 72.

Similarly, the second tine assembly 70 has a second base 98 and a plurality of tines 100 that extend radially outwardly from the base 98. The tines 100 are also pivotally connected to the base 98. A blade 102 is provided on the distal end of each tine 100. The blades 102 engage or grip against the inner wall 22 of the syringe barrel 16. In addition, a second tine spring 104 is connected to the second tines 100. The second tine spring 104 biases and pulls the second tines 100 against the inner wall 22 of the syringe barrel 16 in the same direction as engine movement. The second base 98 further has an inner annular groove 103 (FIG. 4) that receives the ball bearings 80 of the ball cage 78 when fully assembled. The second base 98 has openings 106 that will cooperate with the front shroud 72 as described below. The second tines 100 do not rotate with the cam assembly 66. The second tines 100 do however move linearly along the syringe barrel 16 and are referred to as "moving tines" 100.

The front shroud 72 has a cylindrical housing 108. A plurality of tie rods 110 extend from the housing 108 and are received through the openings 106 on the second base 98. The second tine assembly 70 moves linearly along the tie rods 110 of the front shroud 72 during operation of the pump 10. The front shroud 72 is fixed to the electronics housing 40 via the tie rods 110. In a preferred embodiment, five tie rods 110 are utilized.

Figure 6:
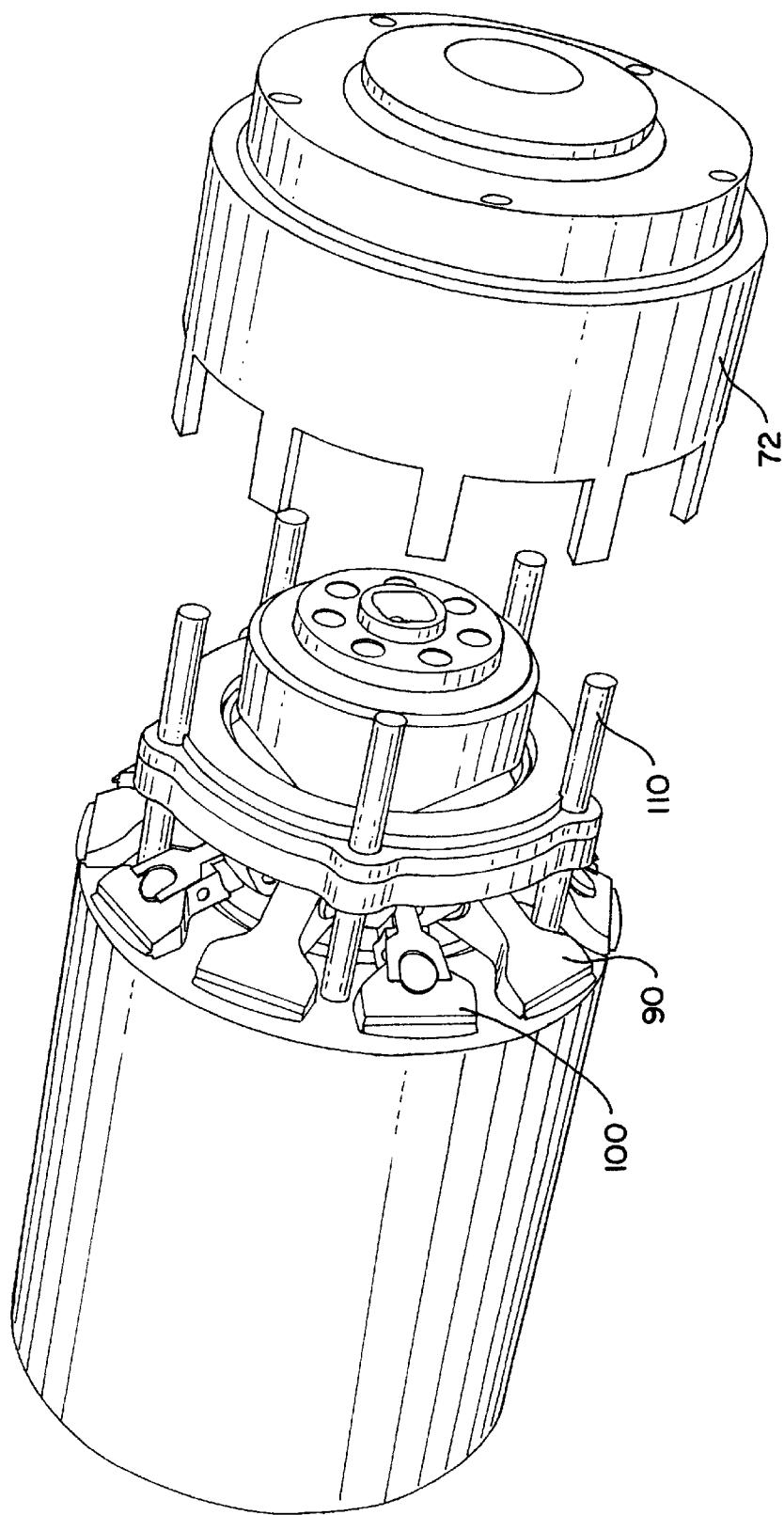
FIG. 6 is an partial exploded perspective view of the reusable infusion engine.

FIG. 6 shows the infusion engine substantially assembled but with the cylindrical housing 108 of the front shroud 72 exploded away. The drive mechanism 44 is secured within the electronics housing 40. The gearbox 52 extends into the motor housing 86 of the first tine assembly 68 wherein the drive connector 54 is secured thereto. The ball bearings 80 of the ball cage 78 ride within the inner groove 103 of the second tine assembly 70 and also ride within the cam groove 76 of the cam member 74. Thus, the second tine assembly 70 is connected to the cam assembly 66. As assembled, the first and second tine assemblies 68,70 are interlaced in nestled fashion. The front shroud 72 covers the cam assembly 66 and the tines 90,100 extend out from a bottom portion of the front shroud 72. Accordingly, the infusion engine 14 is fully assembled.

As shown in FIG. 1, to prepare the pump 10 for use, appropriate I.V. tubing (not shown) is prepared for intravenous delivery to a patient. Of course the pump 10 can also be used to deliver nutritional products or peritoneal dialysis solutions to a patient as is well known in the art without departing from the invention. The syringe barrel 16 is first filled with a predetermined amount of medicament based on the desired therapy. A removable handle molding (not shown) is provided so that the syringe 12 can be filled in the conventional manner. At this point, the luer cap may be positioned over the opening 28. The appropriate smart card 44 is inserted into the slot 62 on the infusion engine 14. The infusion engine 14 is then inserted into the open end of the barrel 16. The start button 56 is pushed on the infusion engine 14. The start button 56 could also be pushed before insertion into the syringe barrel 16 as there is an adequate time delay before the engine 14 will begin to advance in the syringe 12. The cap 18 is then screwed onto the syringe barrel 16. The tamper evident tab will engage. The I.V. tubing is connected to the syringe barrel 16 and to the patient for intravenous delivery. The infusion engine 14 will advance to the plunger 17 and be ready for infusion therapy. The smart card 44 determines the drug infusion rate. The card 44 would contain either a standard therapy program or a custom clinician programmed card prepared by medical personnel. It is further noted that the syringe 12 is designed such that the smart card 44 can be visible through the syringe 12 wall. The visible portion of the smart card 44 will show the patient's name and infusion rate.

When the infusion engine 14 is inserted into the syringe 12, the plunger detect sensor 64 should sense that the infusion engine 14 is abutted against the plunger 17. If the start button 56 on the engine 14 is pushed, but the infusion engine does not detect the presence of the plunger 17, the infusion engine 14 is advanced (through activation of the pump head 42 components as described below) at a fast forward speed, until the sensor 64 detects the plunger 17. Once this occurs, the engine 14 will revert to the programmed infusion rate as determined by the smart card 44.

Figure 7:
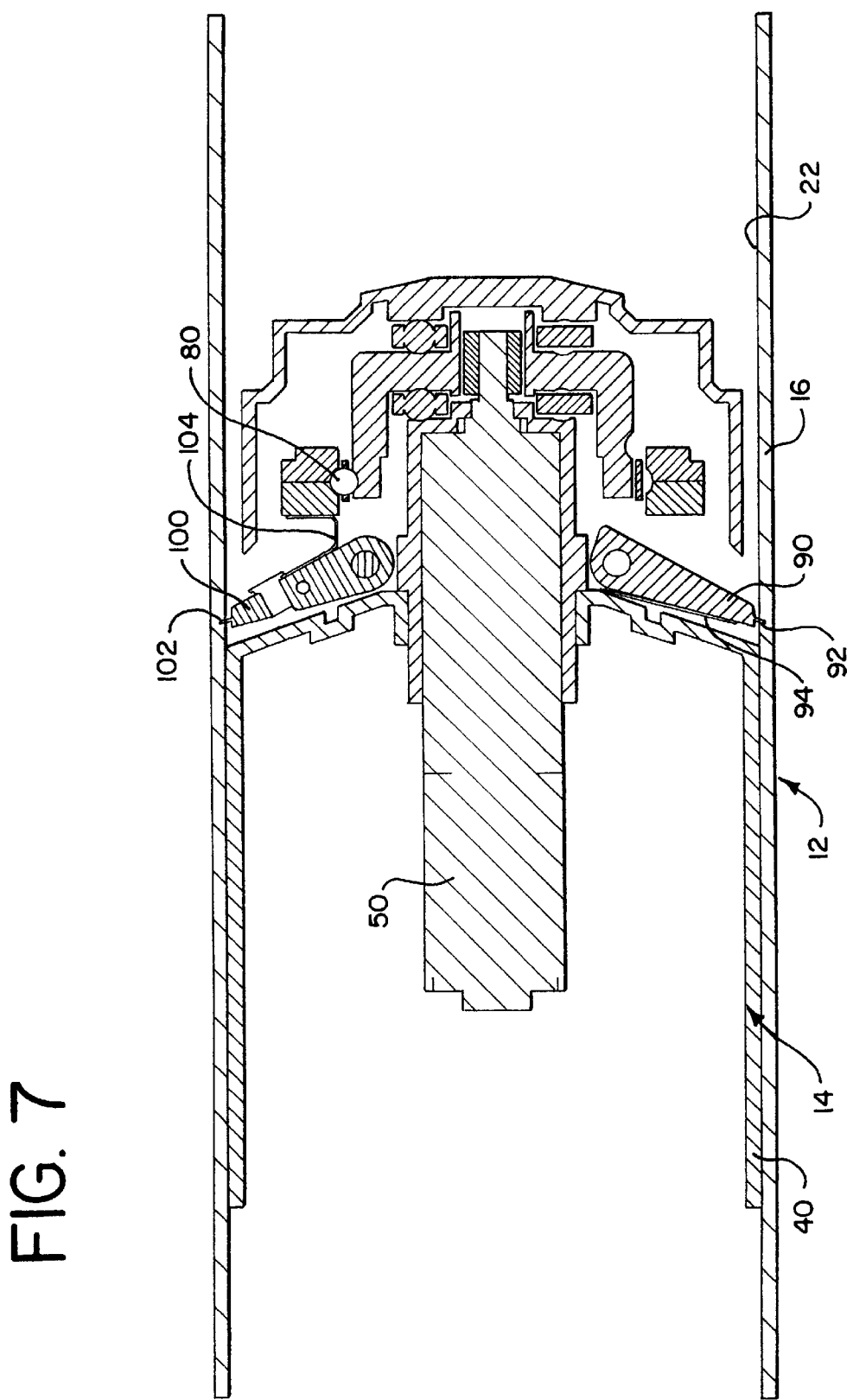
FIG. 7 is a partial cross-sectional view of the infusion pump of FIG. 1.

FIGS. 7–12 disclose operation of the pump 10 during infusion therapy. FIG. 7 discloses the infusion engine 14 in sliding engagement with the syringe 12. For clarity, certain parts are not shown in FIG. 7. In general, the infusion engine 14 moves in incremental steps along the inner wall 22 of the syringe barrel 16, i.e. the infusion engine 14 "walks" along the syringe 12. One step is defined as an infusion cycle.

Figure 8:
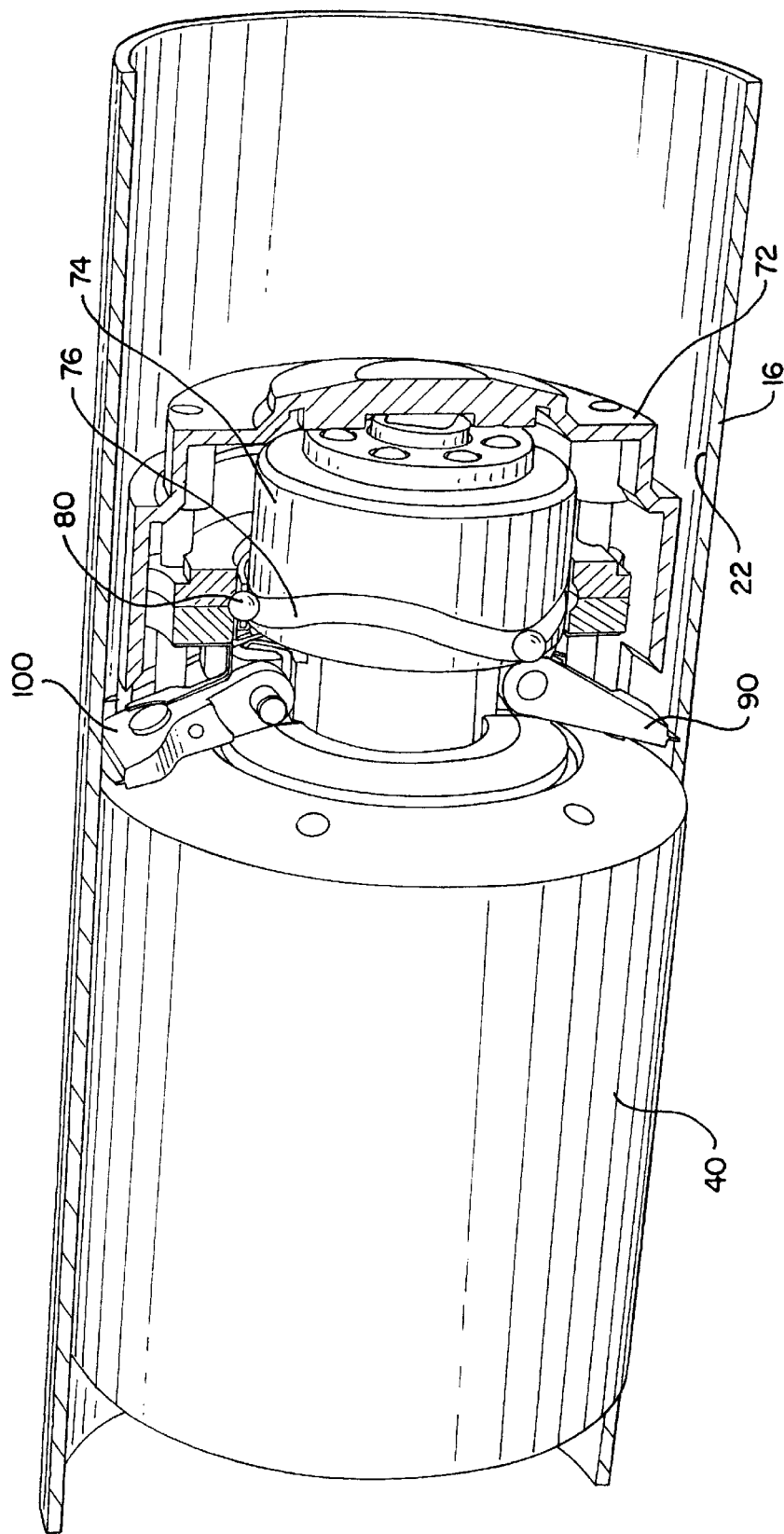
FIG. 8 is a partial cross-sectional view showing the pump at a start of an infusion cycle.
Figure 9:
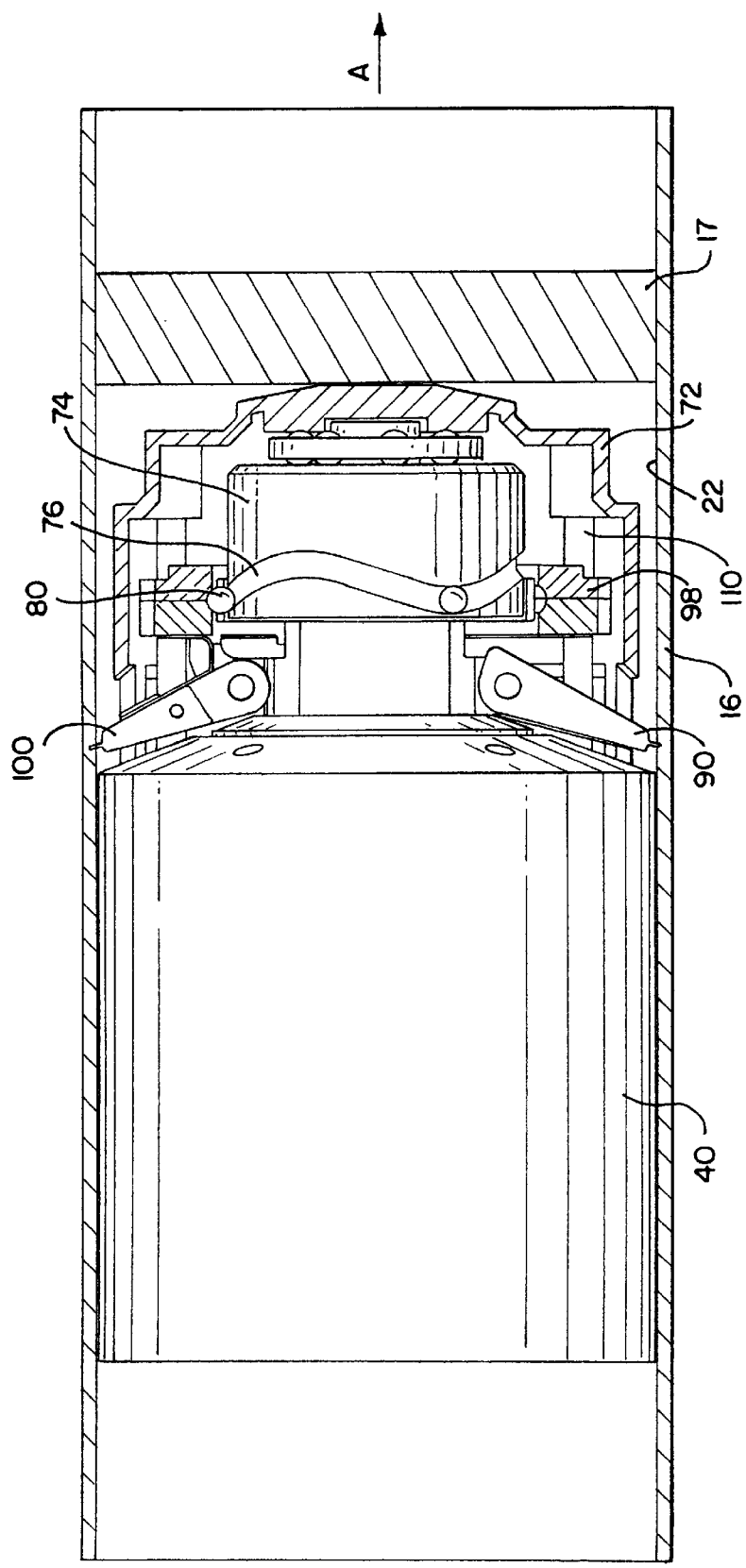
FIG. 9 is a cross-sectional view of the pump at the start of the infusion cycle.
Figure 11:
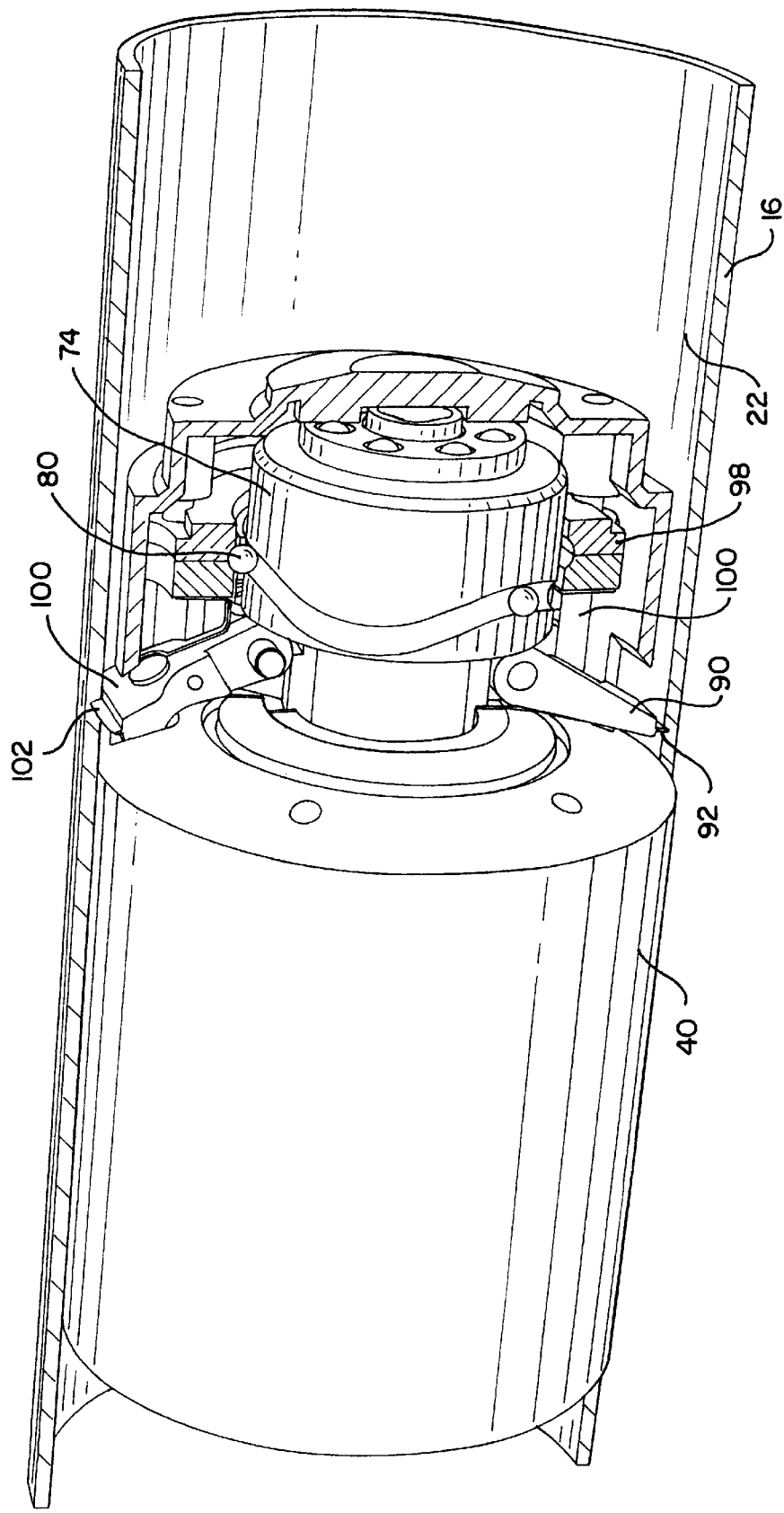
FIG. 11 is a partial cross-sectional view showing the pump at the end of the infusion cycle.

As explained below, the components of the infusion engine 14 perform several different movements to linearly move the engine 14. The infusion engine travels several steps and, therefore, completes several infusion cycles to travel the required length of the syringe barrel 16 to complete an infusion therapy. FIGS. 8–10 disclose the infusion engine at a start of the infusion cycle. The first tines 90 of the first tine assembly 68 are engaged against the inner wall 22 of the syringe barrel 16. Likewise, the second tines 100 of the second tine assembly 70 are engaged against the inner wall 22 of the syringe barrel 16. The ball bearings 80 on the ball cage 78 are nestled in the cam groove 76 at a bottom portion of the sinusoidal shape of the cam groove 76. This position defines an infusion start position. The drive mechanism 44 of the engine 14 is pulsed wherein the drive mechanism 44 rotates in one direction therefore rotating the cam member 74. As the cam member 74 rotates, the ball bearings 80 roll upward along the cam groove 76. Because the first tines 90 are forced against the syringe barrel 16 in a locking fashion, any movement of the infusion engine 14 along the syringe barrel 16 towards the cap 18 end of the syringe 12 is prevented. Thus, the first tine assembly 68 remains linearly stationary. As the ball cage is connected to the second tine assembly 70 via the annular groove 103, this forces the assembly 70 and the second tines 100 linearly along the inner surface of the syringe barrel 16, only with a slight dragging force from the angle configuration of the tines 100 and the biased position of the tines 100. During this movement, the second tine assembly 70 moves along the tie rods 110 on the front shroud 72.

In a preferred form of the invention shown in FIG. 12b, movement of the ball bearings 80 from a bottom of the groove 76 to the top, or crest of the groove 76 results in linear movement of the second tine assembly 70 and the front shroud 72 of 2.5 mm. The movement requires 60 degrees of rotation of the cam member 74. Thus, 60 degrees of rotation of the cam member 74 moves the ball bearings 80 from a bottom to the top of the sinusoidal shape of the cam groove 76. As the front shroud 72 abuts the plunger 17, the plunger also linearly moves 2.5 mm along the syringe barrel 16. This linear movement thus displaces medicament from the syringe 12, through the appropriate I.V. tubing, and into the patient. Accordingly, as the ball bearings 80 run up the cam groove 76 via rotational movement of the cam member 74, this motion is converted to linear movement of the second tine assembly 70. It is this fundamental linear motion of the second tine assembly 70 that is used to "walk" the infusion engine 14 down the syringe 12, hence moving the plunger 17 and displacing medicament from the syringe 12 and into the patient. As shown in FIG. 9, the infusion engine 14 moves the plunger 17 in an infusion direction represented by the arrow A.

Before the infusion engine 14 can complete another infusion cycle, the engine 14 must reset. To reset, the drive mechanism 44 pulses again and further rotates the cam member 74 in the same direction. The ball bearings 80, now at the top of the sinusoidal cam groove 76, move down the sinusoidal cam groove 76 to the bottom position. This movement biases the second tine assembly 70 back towards the first tine assembly 68. Because the second tines 100 are biased against and engaged with the inner wall 22 of the syringe barrel 16, the second tine assembly 70 is prevented from movement back towards the first tine assembly 68 and thus remains stationary. The tines 90 of the first tine assembly 68, however, can slide along the inner wall 22 of the syringe barrel 16. Accordingly, the path of least resistance is for the electronics housing 40, first tine assembly 68 and cam assembly 66 to linearly move towards the stationary second tine assembly 70. Thus, the infusion cycle and the reset cycle results in the infusion engine 14 "inching" or "walking along" the syringe barrel 16. The end of the reset cycle places the pump 10 at a start of a next infusion cycle. The reset cycle also requires approximately 60 degrees of rotation.

The drive mechanism 44 is pulsed again and the infusion engine 14 completes another infusion cycle. A complete revolution of the cam member 74 (360 degrees) comprises three sets of an infusion cycle (60 degrees) and a reset cycle (60 degrees). The infusion cycles and reset cycles are continued according to the instructions from the smart card until the infusion therapy is complete. For example, the infusion therapy typically is designed to be complete when the plunger 17 bottoms out against an end wall of the syringe 12. When this occurs, the engine 14 will be unable to move and the motor 50 will begin to stall. The electronics associated with the motor 50 will detect an increased current draw and will then shut down the infusion therapy process.

As can be appreciated, the tines 90,100 are designed to a particular length and assembled at an angle such that when the infusion engine 14 travels down the syringe 12, there is a very low drag force of the blades 92,102 moving in frictional engagement along the inner wall 22 of the syringe barrel 16. The design of the tines 90,100, however is such that if a force in the opposite direction (i.e., towards the end cap 18), such as back pressure applied to the plunger 17, the tines 90,100 will "lock-out" and will not allow the engine 14 to "back-drive" back up the syringe 12.

In a preferred form of the invention, the tines 90,100 can resist up to approximately 50 lbs. in force. Thus, the tines 90,100 of the first and second tine assemblies 68,70 prevent movement of the infusion engine 14 toward the end cap 18 of the syringe 12. Thus, during operation, the infusion engine 14 can only move towards the first end 24 of the syringe barrel 16 having the opening 28.

A spring release mechanism is provided to allow the infusion engine 14 to be removed from the syringe barrel 16 once it has advanced the plunger to the first end 24 of the syringe 12. A mechanism is provided such that the tines 90,100 of the first and second tine assemblies 68,70 are biased towards the electronics housing 40. This releases the blades 92,102 of the tines 90,100 from the inner wall 22 of the syringe barrel 16. In this "spring release position," the infusion engine 14 can then be removed from the syringe barrel 16. The cap 18 is removed and the syringe barrel 16 is tipped up to allow the engine 14 to slide out of the syringe barrel 16. The cap 18 and syringe barrel 16 are then disposed of accordingly. The battery pack 46 on the infusion engine 14 can be removed from the engine 14 and recharged in a docking station, or another smart card 44 can be placed into the engine 14 wherein the engine 14 can be used again for another infusion therapy (provided the battery status indicates it has enough charge to complete another complete therapy).

Figure 4A:
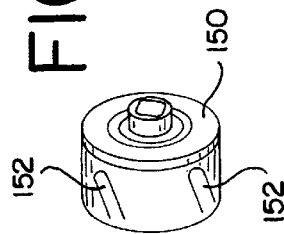
FIG. 4a is a perspective view of alternative embodiment of a cam member of a cam assembly of the present invention.
Figure 5:
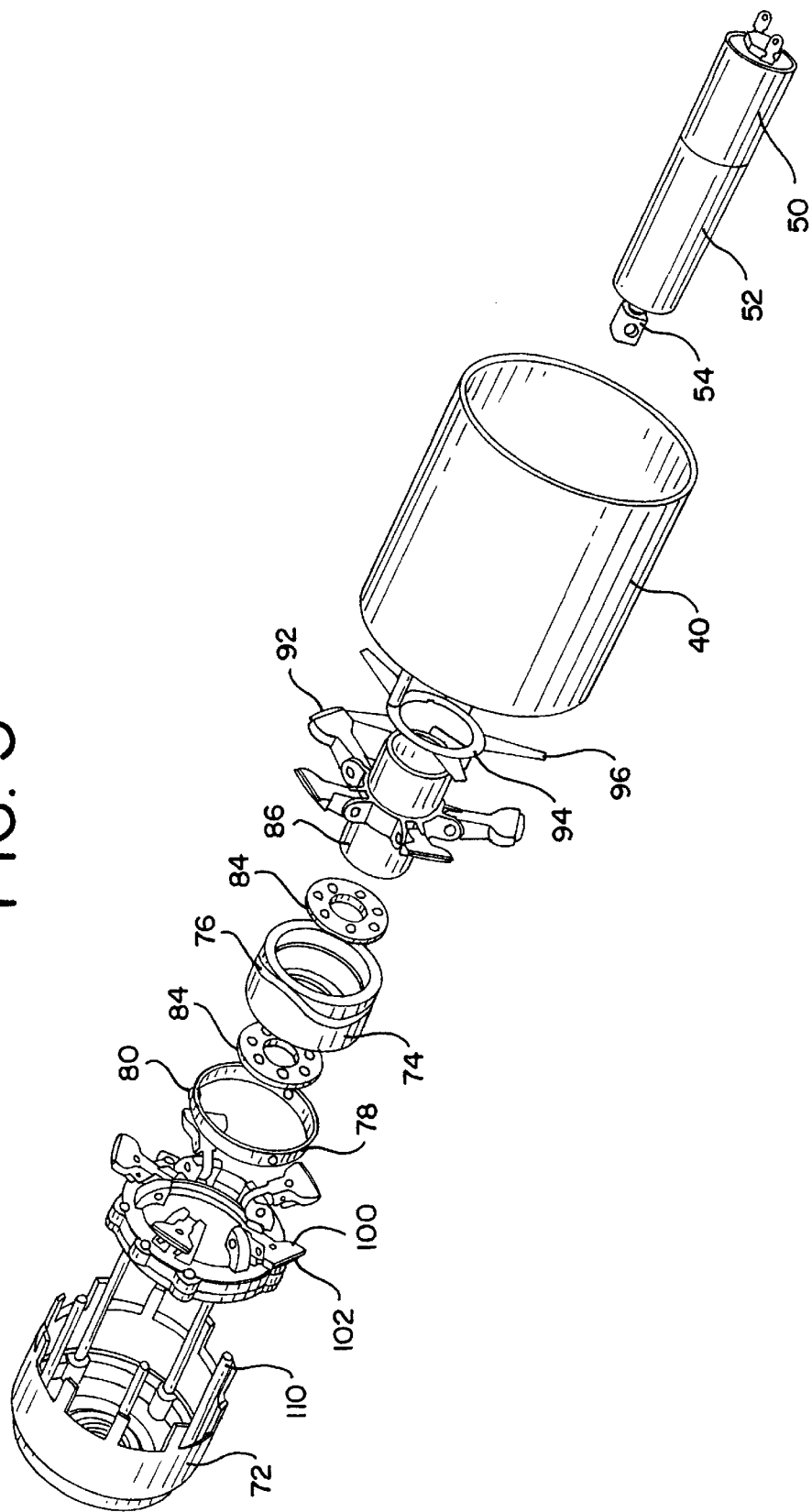
FIG. 5 is a more detailed rear exploded perspective view of the pump of FIG. 1.

As can be appreciated, the cam assembly 66 can take other forms. FIG. 4a shows another cam assembly 66 but having a cam member 150 that is structured differently from the cam member 74. The cam member 150 has a cam groove 152 that is helically-shaped along the cam member 150. In a preferred embodiment, the cam member 150 has three cam grooves 152. This cam member 150 thus moves the second tine assembly 70 in a similar fashion as cam member 74. To perform the reset cycle, however, the drive mechanism 44 pulses the cam member 150 in the opposite direction wherein the ball bearings 80 ride back down the cam groove 152.

FIGS. 13–17 show another embodiment of the ambulatory infusion pump of the present invention. The pump 200 generally includes a syringe assembly 212 and an infusion engine 214. Like the infusion engine 14 of the pump 10, the infusion engine 214 of this embodiment also "walks along" the syringe assembly 212. This infusion engine 214, however, has a different mechanism for moving the engine 214 along the syringe assembly 212.

The infusion engine 214 has a drive mechanism similar to the infusion engine 14. The infusion engine further includes, however, a disc drive assembly 220 that walks the engine 214 along the syringe 212. The disc drive assembly 220 generally includes a lead screw 222, a first disc assembly 224 and a second disc assembly 226. The lead screw 222 has a first portion 228 and a second portion 230. The first portion 228 has threads in one direction (e.g. left-hand threads) and the second portion 230 has threads in an opposite direction (e.g. right-hand threads). The first disc assembly 224 has a first disc 232 and a plurality of first tines 234. The second disc assembly 226 has a second disc 236 and a plurality of second tines 238. The first disc 232 has threads and fits over the first portion 228 of the lead screw 222, and the second disc 236 has threads and fits over the second portion 230 of the lead screw 222.

Figure 15:
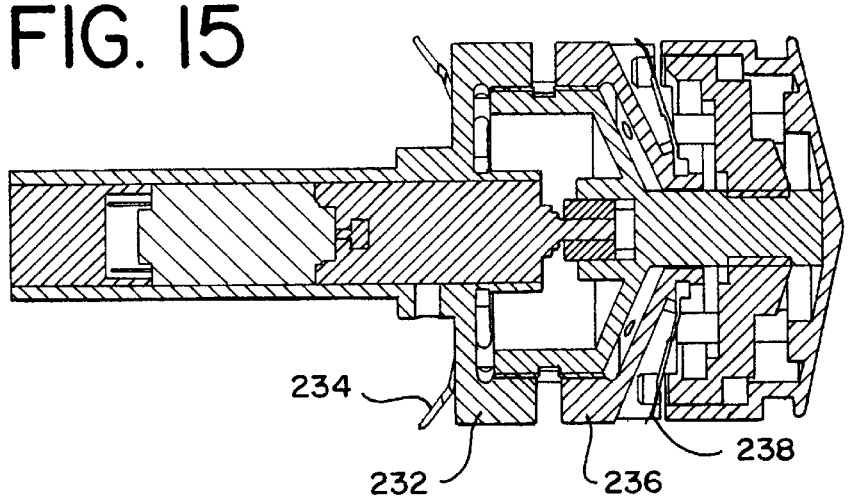
FIG. 15 is a cross-sectional view of the infusion engine of the pump of FIG. 12 at the start of the infusion cycle.
Figure 16:
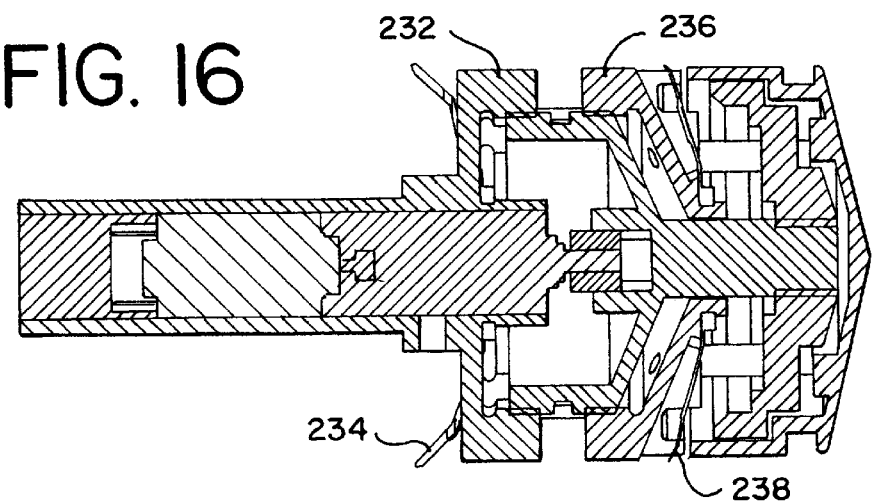
FIG. 16 is a cross-sectional view of the infusion engine of the pump of FIG. 12 at the end of the infusion cycle.
Figure 17:
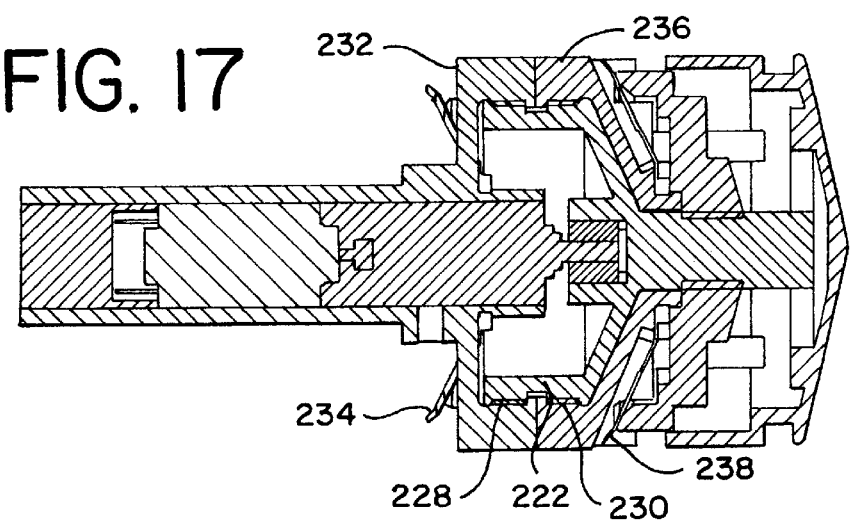
FIG. 17 is a cross-sectional view of the infusion engine of the pump of FIG. 12 at the end of the infusion cycle in a spring release position.

As shown in FIGS. 15 and 16, when the drive mechanism pulses and turns the lead screw 222 in one direction, the discs 232,236 turn and are forced away from each other. Similar to the previous embodiment, the first tines 234 engage the syringe 212 and lock-out. Thus, the second disc assembly 226 moves along the syringe 212 wherein the second tines 238 slide along an inner wall of the syringe 212. Similar to the description above, this movement pushes a plunger 240 within the syringe 212 to displace medicament into the patient. Thus, an infusion cycle is completed. The engine 214 must now be reset. To reset, the drive mechanism pulses to turn the lead screw 222, but in the opposite direction. This forces the disc assemblies 224,226 towards one another. The second tines 238 lock-out against the syringe 212 preventing movement. Thus, the first disc assembly 224 and therefore, the remaining components of the infusion engine 214 move towards the second disc assembly 226. Now the pump 200 is ready for the next infusion cycle. The rotary movement of the lead screw 222 results in the linear movement, or the walking of the infusion engine 214 along the syringe 212. FIG. 17 shows the spring release position at the end of infusion therapy wherein the lead screw 222 is turned such that the discs 232,236 come together and bias the tines 234,238 away from engagement from the syringe 212. In this position, the infusion engine 214 can be removed from the syringe 212.

The infusion pump of the present invention can incorporate many different configurations wherein the infusion pump can linearly move, or walk, along the syringe assembly. Other configurations include a motorized wheel assembly that could ride along tracks positioned on the inner wall of the syringe barrel. A mini-hydraulic system could also be employed. A solenoid system could also be employed. An articulated arm that grips the syringe could also be used.

It is understood that in a preferred embodiment, the tines 90,100 engage or grip the inner wall 22 of the syringe barrel 16. It is understood that the infusion engine 14 can have engaging members that engage or grip other portions of the syringe 12 or other components associated with the syringe, for moving therein. For example, the syringe 12 could be equipped with longitudinal rods wherein the engine 14 grips and moves along the rods. The rods could pass through openings provided for in the engine 14 or be fully encapsulated therein.

Thus, the present invention provides an extremely lightweight and portable ambulatory infusion pump. Because the infusion engine 14 walks down the syringe 12 by it own mechanism, no external linkage is required to drive the plunger as is typically required in prior art pumps (See FIG. 18). This eliminates the need for an additional outer case for the pump 10. The syringe assembly 12 itself serves as the case for the entire pump 10 making it more compact and easier to be worn by the patient.

Figure 18:
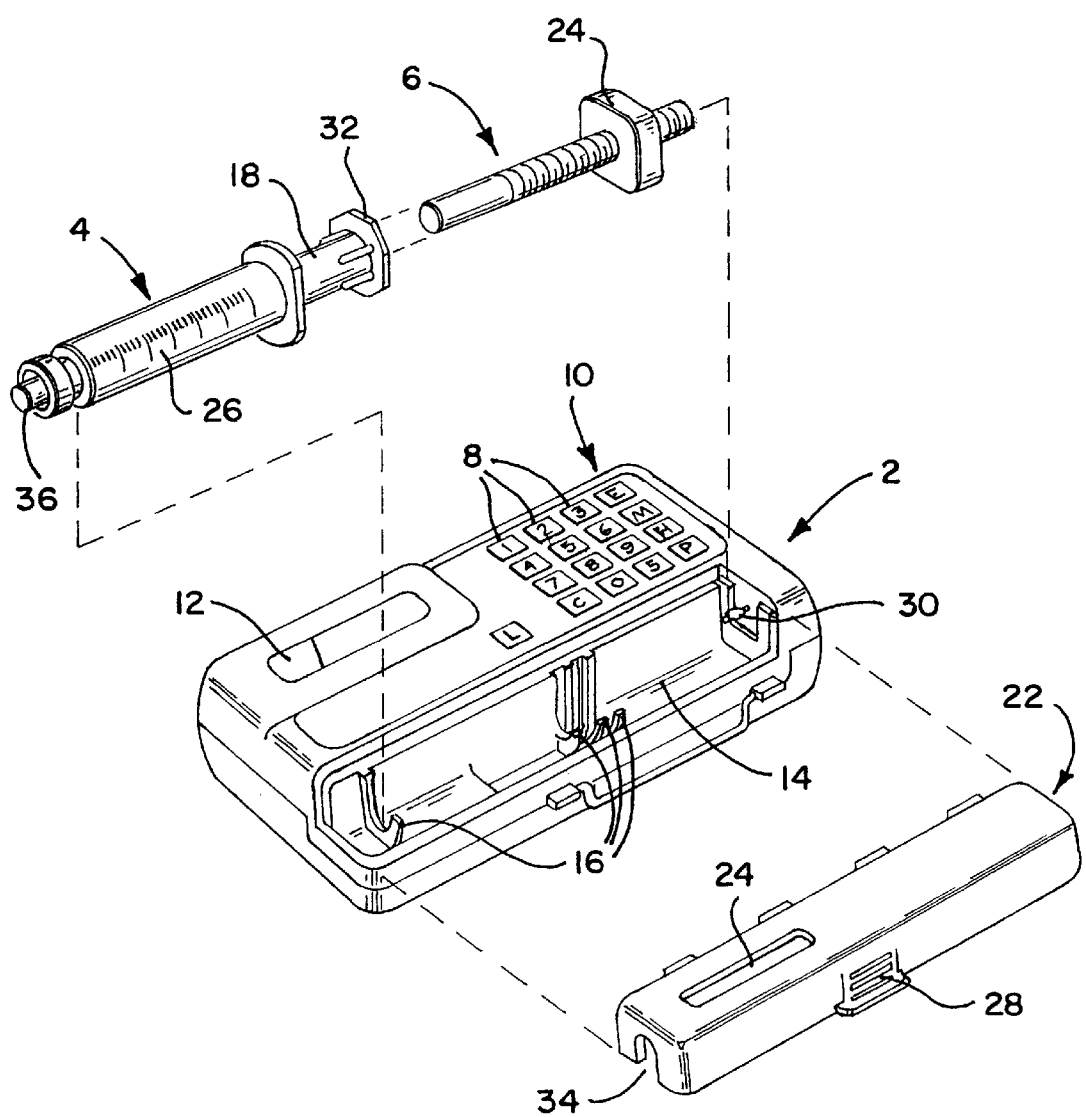
FIG. 18 is an exploded perspective view of a prior art ambulatory infusion pump.

As discussed, prior art syringe-based infusion pumps, such as shown in FIG. 18, require an external linkage to be attached to the plunger in order to move the plunger along the required length of the syringe. This adds to the overall length of the pump. In the present invention, the syringe barrel 16 defines the fluid chamber 19 which has a first length L1. The infusion engine 14 has a second length L2. Unlike prior art devices, the length L2 is less than the length L1. In prior art devices, the length of the plunger mechanism, i.e., the plunger and extension arm that pushes the plunger, is required to be at least the length of the fluid chamber in order to fully evacuate the fluid chamber. In the present invention, the infusion engine linearly moves on its own and thus, does not require an external connection. Instead, the infusion engine 14 is self-propelled within the syringe 12. Thus, the walking infusion engine 14 allows for the length of the engine 14 to be less than the length of the syringe barrel 16 defining the fluid chamber. The pump 10 does not require structure to extend from the syringe barrel 16 to serve as a force applying and transmitting surface. This is unnecessary because the infusion engine, once inserted into the syringe 12 linearly moves without an external force being applied from outside of the syringe 12.

Furthermore, because the infusion engine has its own mechanism to linearly move along the syringe to displace fluid, the infusion engine can be entirely located within the syringe barrel. This also allows for an end cap that can completely and securely close the syringe 12 in liquid-tight fashion.

While the specific embodiments have been illustrated and described, numerous modifications come to mind without significantly departing from the spirit of the invention, and the scope of protection is only limited by the scope of the accompanying Claims.

We claim:

1. An infusion pump for a syringe barrel having a fluid chamber and an inner wall surface, the pump comprising:
   an infusion engine having an electric motor for moving fluid through the syringe barrel, the engine having a member adapted to engage a portion of the syringe barrel for moving the engine linearly along the syringe barrel.

2. The pump of claim 1 wherein the engine is adapted to be positioned entirely within the syringe barrel.

3. The pump of claim 1 wherein the member is adapted to engage the inner wall to move the engine linearly along the syringe barrel.

4. The pump of claim 3 wherein the member is a tine.

5. The pump of claim 4 wherein the member is a plurality of circumferentially spaced tines.

6. The pump of claim 1 wherein the engine comprises a battery for operating the electric motor, and a pump head.

7. The pump of claim 1 wherein the fluid chamber is adapted to have a first length and the engine has a second length wherein the second length is less than the first length.

8. An infusion pump for a syringe barrel having a fluid chamber and an inner wall surface, the pump comprising:
an infusion engine having an electric motor and wall engaging members adapted for moving the engine through the syringe barrel, the engine being entirely located within the fluid chamber.

9. The pump of claim 8 wherein the member is a tine.

10. The pump of claim 9 wherein the member is a plurality of circumferentially spaced tines.

11. The pump of claim 8 wherein the engine comprises a battery for operating the electric motor, and a pump head.

12. The pump of claim 8 wherein the fluid chamber is adapted to have a first length and the engine has a second length wherein the second length is less than the first length.

13. The pump of claim 1 wherein the pump is an ambulatory infusion pump.

14. An infusion pump comprising:
a syringe barrel having a fluid chamber and an inner wall surface; and
means for moving fluid through the syringe barrel the means being positioned entirely within the fluid chamber.

15. The pump of claim 14 wherein the means for moving fluid is an infusion engine.

16. The pump of claim 15 wherein the engine comprises a motor and a member for engaging the syringe barrel for moving the engine linearly through the fluid chamber.

17. The pump of claim 16 wherein the member engages the inner wall surface to move the engine linearly through the syringe barrel.

18. The pump of claim 17 wherein the member is a tine.

19. The pump of claim 18 wherein the member is a plurality of circumferentially spaced tines.

20. The pump of claim 16 wherein the fluid chamber has a first length and the engine has a second length wherein the second length is less than the first length.

21. A pump engine for moving fluid through a fluid chamber of a syringe barrel, the engine comprising:
a motor having a shaft;
a first member connected to the shaft for engaging a portion of the syringe barrel;
a second member for engaging a portion of the syringe barrel;
a third member connected to the shaft the second member connected to the third member and being responsive to rotation of the shaft to cause the second member to move linearly independently of the first member.

22. The engine of claim 21 wherein the first member is a tine.

23. The engine of claim 22 wherein the second member is a tine.

24. The engine of claim 21 wherein the first member is a plurality of circumferentially spaced tines.

25. The engine of claim 21 wherein the third member is a cam member responsive to rotation of the shaft to cause the engine to move linearly through the fluid chamber.

26. The engine of claim 25 wherein the cam member is a cylindrical drum having a circuitous groove on an outer surface.

27. The engine of claim 25 wherein the cam member is a cylindrical drum having a first portion with right-handed threads and a second portion with left-handed threads.

28. The pump engine of claim 21 where upon further rotation of the shaft, the first member moves linearly along the syringe barrel independently of the second member.

29. A method for infusing a fluid to a patient comprising:
providing a syringe barrel having a fluid chamber and an infusion direction;
providing an infusion engine having an electric motor and a member for engaging a portion of the syringe barrel;
positioning the infusion engine within the syringe barrel; and
driving the engine linearly within the fluid chamber by moving the member into operative engagement with a portion of the syringe barrel.

30. The method of claim 29 wherein the member has a first portion and a second portion, wherein the step of driving the engine comprises the steps of:
a first step of moving the second portion in the infusion direction while the first portion remains stationary; and
a second step following the first step of moving the first portion in the infusion direction while the second portion remains stationary.

31. The method of claim 30 wherein the first portion is a first tine.

32. The method of claim 31 wherein the second portion is a second tine.

33. An infusion pump comprising:
a syringe barrel having a first length;
an infusion engine having a cam assembly positioned within the syringe barrel and being linearly movable along the syringe barrel; the infusion engine having a second length, the second length being less than the first length.

34. The infusion pump of claim 33 further comprising a plunger positioned adjacent the infusion engine wherein the infusion engine and plunger define the second length.

35. An infusion pump for a syringe barrel having a fluid chamber and an inner wall, the syringe barrel having an opening to allow for fluid to be displaced therethrough, the infusion pump comprising:
an infusion engine adapted to be positioned within the syringe barrel, the infusion engine comprising:
a motor;
a cam member connected to the motor for rotation by the motor, the cam member having a cam groove having a first portion;
a first member connected to the motor and adapted for engaging the inner wall;
a second member adapted for engaging the inner wall and being positioned to ride along the cam groove;
wherein the motor rotates the cam member wherein the first member is adapted to locks against the inner wall and wherein the second member rides along the first portion of the cam groove wherein the second member is adapted to moves linearly along the syringe barrel in an infusion direction to define an infusion cycle wherein fluid is displaced from the fluid chamber.

36. The infusion pump of claim 35 wherein the cam groove has a second portion and upon further rotation of the motor, the second member rides along the second portion wherein the second member is adapted to locks against the inner wall and the first member, cam member and motor are adapted to move linearly along the syringe barrel in the infusion direction to define a reset cycle.

37. The infusion pump of claim 36 wherein the motor further rotates to complete a plurality of infusion cycles and reset cycles wherein the infusion engine is adapted to walks along the syringe barrel to displace fluid from the syringe barrel.

38. The infusion pump of claim 35 wherein the syringe barrel is adapted to have a first length and the infusion engine has a second length, the second length being less than the first length.

39. The infusion engine of claim 35 further comprising a plunger positioned adjacent the infusion engine wherein the infusion engine and plunger define the second length.

40. The infusion pump of claim 35 wherein the infusion engine is adapted to be positioned entirely within the syringe barrel.

41. The infusion engine of claim 35 wherein the first portion of the cam groove is an upward portion and the second portion of the cam groove is a downward portion.

42. The infusion pump of claim 35 wherein the cam groove is generally sinusoidal in shape.

43. The infusion pump of claim 35 wherein the first member is a first tine assembly connected to the motor, the first tine assembly having a plurality of first tines adapted to engage the inner wall.

44. The infusion pump of claim 35 wherein the second member is a second tine assembly having a plurality of second tines engaging adapted to engage the inner wall, the second tine assembly having a bearing assembly positioned to ride along the cam groove.

45. The infusion pump of claim 35 further comprising a plunger adapted to be positioned within the syringe barrel and engaged by the infusion engine.

46. The infusion engine of claim 45 further comprising a shroud positioned over the first and second members, the shroud engaging the plunger.

47. The infusion engine of claim 35 wherein the syringe barrel is adapted to have an end cap releasably secured to the syringe barrel wherein the infusion engine is completely enclosed within the syringe barrel.

48. The infusion engine of claim 43 further comprising a first spring connected to the first tines and adapted to bias the first tines against the inner wall.

49. The infusion engine of claim 44 further comprising a second spring connected to the second tines and adapted to bias the second tines against the inner wall.

50. An infusion pump for a fluid container having an inner wall surface, the pump comprising a self-propelled plunger having a motile source contained entirely within the container, the self-propelled plunger adapted to linearly move along the inner wall surface wherein fluid contained within the fluid container is displaced from the container.

51. The pump of claim 50 wherein the plunger moves along the inner wall surface by engaging the inner wall surface.

52. The pump of claim 50 wherein the self-propelled plunger is positioned entirely within the fluid container.

53. An infusion pump for a syringe barrel having an inner wall surface, the infusion pump comprising:
   a plunger adapted to be positioned in surface-to-surface engagement with the inner wall surface; and
   means for advancing the plunger along the inner wall surface, the means being positioned entirely within the syringe barrel.

54. An infusion pump for a fluid container having an inner wall surface, the pump comprising an infusion engine having an electric motor, the infusion engine adapted to walk along the inner wall surface and displace fluid from the fluid container.

55. An ambulatory infusion pump comprising:
a syringe barrel having a fluid chamber and an inner wall, the syringe barrel having an opening to allow for fluid to be displaced therethrough;
a plunger positioned within the syringe barrel;
a motor positioned within the syringe barrel;
a cam member connected to the motor for rotation by the motor, the cam member having a cam groove having an upward portion and a downward portion;
a first tine assembly connected to the motor, the first tine assembly having a plurality of first tines engaging the inner wall;
a second tine assembly having a plurality of second tines engaging the inner wall, the second tine assembly having a bearing positioned to ride along the cam groove, the second tine assembly positioned adjacent the plunger;
an end cap releasably secured to the syringe barrel;
wherein the motor rotates the cam member wherein the first tines lock against the inner wall and wherein the bearing assembly rides along the upward portion of the cam groove wherein the second tine assembly moves linearly along the syringe barrel in an infusion direction thereby moving the plunger along the syringe barrel to define an infusion cycle wherein fluid is displaced from the fluid chamber,
and wherein the motor further rotates the cam member wherein the bearing assembly rides along the downward portion of the cam groove wherein the second tines lock against the inner wall and the first tine assembly, cam member and motor move linearly along the syringe barrel to define a reset cycle.

56. An ambulatory infusion pump comprising:
a syringe barrel having a fluid chamber and an inner wall, the syringe barrel having an opening to allow for fluid to be displaced therethrough;
a plunger positioned within the syringe barrel;
a motor positioned within the syringe barrel;
a screw having a first portion and a second portion, the first portion having threads in a first direction, the second portion having threads in a second direction generally opposite to the first direction;
a first disc assembly having a first disc and a plurality of first tines, the first disc having threads cooperating with the first portion threads, the first tines engaging the inner wall;
a second disc assembly having a second disc and a plurality of second tines, the second disc having threads cooperating with the second portion threads, the second tines engaging the inner wall, the second disc assembly positioned adjacent the plunger;
an end cap releasably secured to the syringe barrel;
wherein the motor rotates the screw in a first direction wherein and the first disc threads cooperate with the first portion threads and the second disc threads cooperate with the second portion threads wherein the discs are forced away from one another wherein the first tines lock against the inner wall and wherein the second disc and second tines moves linearly along the syringe barrel in an infusion direction thereby moving the plunger along the syringe barrel to define an infusion cycle wherein fluid is displaced from the fluid chamber;

and wherein the motor rotates the screw in a second direction opposite the first direction wherein the discs are forced towards one another wherein the second tines lock against the inner wall and the first disc assembly, screw and motor move linearly along the syringe barrel to define a reset cycle.

57. An ambulatory infusion pump comprising:

a syringe barrel having a fluid chamber and an inner wall surface; and an infusion engine having an electric motor positioned entirely within the syringe barrel having a fixed length and wall engaging members for moving the engine through the syringe barrel.

58. An ambulatory infusion pump comprising:

a syringe barrel having a fluid chamber and an inner wall surface; and an infusion engine for moving a fluid through the syringe barrel, the engine having wall engaging members for moving the engine through the syringe barrel and wherein the engine has an electric motor, and converts electrical energy to mechanical energy.

59. An ambulatory infusion pump comprising:

a syringe barrel having a fluid chamber and an inner wall surface; and an infusion engine for moving a fluid through the syringe barrel, the engine having wall engaging members for moving the engine through the syringe barrel wherein the engine includes a drive mechanism wherein rotary movement is converted into linear movement and the entire engine moves simultaneously in a linear direction through the syringe barrel.

60. An infusion pump for use with a syringe having a chamber comprising an infusion engine having a motile source, the infusion engine and motile source contained entirely within the chamber of the syringe.

61. An ambulatory infusion pump comprising:

a syringe barrel having a fluid chamber, and an infusion engine contained within the syringe barrel for moving a fluid through the syringe barrel, the infusion engine including a drive mechanism wherein rotary movement is converted to linear movement.

62. The ambulatory infusion pump of claim 61 wherein rotary movement in a first direction moves a first set of wall engaging members linearly into the syringe barrel, and rotary movement in an opposite direction moves a second set of wall engaging members to reset the infusion engine.

63. An ambulatory infusion pump comprising:

a syringe barrel having a fluid chamber, and an infusion engine contained entirely within the syringe barrel for moving fluid through the syringe barrel, the infusion engine including a drive mechanism having a cam assembly for effecting movement of the infusion engine through the syringe barrel.

64. The ambulatory infusion pump of claim 63 wherein the cam assembly includes a sinusoidal cam groove for effecting movement of wall engaging members connected to the infusion engine.

65. The ambulatory infusion pump of claim 63 wherein the infusion engine includes a power source that is contained entirely within the syringe barrel.

66. An ambulatory infusion pump comprising:

a syringe barrel having a fluid chamber, and an infusion engine contained entirely within the syringe barrel for moving fluid through the syringe barrel, the infusion engine including a drive mechanism controlled by a computer program.

67. The ambulatory infusion pump of claim 66 wherein the infusion engine includes a slot to accept a programmable computer card.

* * * * *